(12) United States Patent
Fong et al.

(10) Patent No.: US 9,402,388 B2
(45) Date of Patent: Aug. 2, 2016

(54) METHODS OF FREEZING STEM CELLS

(71) Applicant: National University of Singapore, Singapore (SG)

(72) Inventors: Chui Yee Fong, Singapore (SG); Tuan Ariffeen Bongso, Singapore (SG); Daniel Hao Lin, Singapore (SG)

(73) Assignee: National University of Singapore, Singapore (SG)

( * ) Notice: Subject to any disclaimer, the term of this patent is extended or adjusted under 35 U.S.C. 154(b) by 95 days.

(21) Appl. No.: 14/069,557

(22) Filed: Nov. 1, 2013

(65) Prior Publication Data

US 2014/0120615 A1 May 1, 2014

Related U.S. Application Data

(60) Provisional application No. 61/721,398, filed on Nov. 1, 2012.

(51) Int. Cl.
*C12N 5/0797* (2010.01)
*A01N 1/02* (2006.01)
*C12N 5/0789* (2010.01)

(52) U.S. Cl.
CPC ............ *A01N 1/0221* (2013.01); *A01N 1/0226* (2013.01); *C12N 5/0647* (2013.01)

(58) Field of Classification Search
None
See application file for complete search history.

(56) References Cited

U.S. PATENT DOCUMENTS

| | | | |
|---|---|---|---|
| 2004/0072259 A1 | 4/2004 | Scadden et al. | |
| 2007/0166825 A1* | 7/2007 | Hatsuyama et al. | 435/372 |
| 2008/0118477 A1 | 5/2008 | Christopherson | |
| 2008/0220520 A1* | 9/2008 | Palecek et al. | 435/374 |
| 2013/0302285 A1 | 11/2013 | Fong et al. | |

FOREIGN PATENT DOCUMENTS

| | | |
|---|---|---|
| KR | 2010-0114729 A | 10/2010 |
| WO | WO 2006/036130 A1 | 4/2006 |
| WO | WO 2007/046775 A1 | 4/2007 |
| WO | WO 2008/060377 A2 | 5/2008 |
| WO | WO 2011/101760 A1 | 8/2011 |
| WO | WO 2011/120535 A1 | 10/2011 |
| WO | WO 2014/027965 A1 | 2/2014 |

OTHER PUBLICATIONS

Mannello & Tonti, "Concise Review: No Breakthroughs for Human Mesenchymal and Embryonic Stem Cell Culture: Conditioned Medium, Feeder Layer, or Feeder-Free; Medium with Fetal Calf Serum, Human Serum or Enriched Plasma; Serum-Free, Serum Replacement Nonconditioned Medium or Ad Hoc Formula?" (2007) Stem Cells: vol. 25: 1603-1609.*

Akino, K., et al., "Human Mesenchymal Stem Cells May Be Involved in Keloid Pathogenesis", *International Journal of Dermatology*, 47(11): 1112-1117 (2008).
Al-Anazi, K., "Autologous Hematopoietic Stem Cell Transplantation for Multiple Myeloma Without Cryopreservation", *Bone Marrow Research*, Article ID 971361: 7 pages (2012).
Ayuzawa, R., et al., "Naïve Human Umbilical Cord Matrix Derived Stem Cells Significantly Attenuate Growth of Human Breast Cancer Cells in Vitro and in Vivo", *Cancer Letters*, 280: 31-37 (2009).
Badiavas, E.V., et al., "Participation of Bone Marrow Derived Cells in Cutaneous Wound Healing", *Journal of Cellular Physiology*, 196: 245-250 (2003).
Badiavas, E.V. and Falanga, V., "Treatment of Chronic Wounds With Bone Marrow-Derived Cells", *Arch Dertmatol*, 139 510-516 (2003).
Baharvand, H., et al., "An Efficient and Easy-To-Use Cryopreservation Protocol for Human ES and iPS Cells", *Nat Protoc*, 5(3): 588-594 (2010).
Bakhshi, T., et al., "Mesenchymal Stem Cells From the Wharton's Jelly of Umbilical Cord Segments Provide Stromal Support for the Maintenance of Cord Blood Hematopoietic Stem Cells During Long-Term Ex Vivo Culture", *Transfusion*, 48(12): 2638-2644 (2008).
Bao, P., et al., "The Role of Vascular Endothelial Growth Factor in Wound Healing", *J Surg Res*, 153(2): 347-358 (2009).
Berz, D., et al., "Cryopreservation of Hemaotpoietic Stem Cells", *American Journal of Hematology*, 82: 463-472 (2007).
Bey, E., et al., "Emerging Therapy for Improving Wound Repair of Severe Radiaiton Burns Using Local Bone Marro-Derived Stem Cell Administrations", *Wound Repair and Regeneration*, 18:50-58 (2010).
Bielefeld, K.A., et al., "Fibronectin and β-Catenin Act in a Regulatory Loop in Dermal Fibroblasts to Modulate Cutaneous Healing", *J Biol Chem*, 286(31): 27687-27697 (2011).
Bissel, M.J. and Radisky, D., "Putting Tumours in Context", *Nat Rev Cancer*, 1(1): 45-54 (2001).
Blankenstein, T., "The Role of Tumor Stroma in the Interaction Between Tumor and Immune System", *Current Opinion in Immunology*, 17: 180-186 (2005).
Blit, P.H. and Jeschke, M.G., "Keloids: Whe Do We Know and What Do We Do Next?", *Transl Res*, 159(3): 173-174 (2012).
Bongso, A. and Fong, C.Y., "The Therapeutic Potential, Challenges and Future Clinical Directions of Stem Cells From Wharton's Jelly of the Human Umbilical Cord", *Stem Cell Rev*, 9(2): 226-240 (2013).
Borue, X., et al., "Bone Marrow-Derived Cells Contribute to Epithelial Engraftment During Wound Healing", *American Journal of Pathology*, 165(5): 1767-1772 (2004).
Brower, J., et al., "Mesenchymal Stem Cell Therapy and Delivery Systems in Nonhealing Wounds", *Advances in Skin & Wound Care*, 24:524-532 (2011).
Broxmeyer, H.E., "Insights Into the Biology of Cord Blood Stem/Progenitor Cells", *Cell Proliferation*, 44: 55-59 (2010).
Bueno, C., et al., The ROCK Inhibitor Y-27632 Negatively Affects the Expansion /Survival of Both Fresh and Cryopreserved Cord Blood-Derived CD34+ Hematopoietic Progenitor Cells, *Stem Cell Rev and Rep*, 6: 215-223 (2010).

(Continued)

*Primary Examiner* — Robert Yamasaki
*Assistant Examiner* — Teresa E Knight
(74) *Attorney, Agent, or Firm* — Hamilton, Brook, Smith & Reynolds, P.C.

(57) ABSTRACT

The invention is directed to a method of freezing stem cells comprising introducing the HSCs into a cell culture medium that has been conditioned with Wharton's Jelly mesenchymal stem cells (WJSCs), thereby producing a stem cell culture, and slowly freezing the stem cell culture. In other aspects, the invention is directed to compositions comprising stem cells produced by the methods provided herein. In yet other aspects, the invention is directed to pharmaceutical compositions comprising the stem cells produced by the methods provided herein.

34 Claims, 11 Drawing Sheets

(56) References Cited

OTHER PUBLICATIONS

Cardone. A., et al., "Prognoostic Value of Desmoplastic Reaction and Lyphocytic Infiltration in the Management of Breast Cancer", *Panminerva Med*, 39(3):174-177 (1997).

Chao, K.C., et al., "Islet-Like Clusters Derived From Mesenchymal Stem Cells in Wharton's Jelly of the Human Umbilical Cord for Transplantation to Control Type I Diabetes" *PlosOne*, e1451: 9 pages (2008).

Chao, K.C., et al., "Human Umbilical Cord Mesenchymal Stem Cells Suppress Breast Cancer Tumourigenesis Through Direct Cell-Cell Contact and Internalization", *J Cell Mol Med*, 16(8): 1803-1815 (2012).

Chen, L., et al., "Analysis of Allogenicity of Mesenchymal Stem Cells in Engraftment and Wound Healing in Mice", *Plos One*, e7119, 4(9): 7 pages (2009).

Chithra, P., et al., "Influence of Aloe Vera on Collagen Characteristics in Healing Dermal Wounds in Rats", *Molecular and Cellular Biochemistry* 181: 71-76 (1998).

Chithra, P., et al., "Influence of Aloe Vera on the Healing of Dermal Wounds in Diabetic Rats", *J Ethnopharmacol*, 56(3): 195-201 (1998).

Clark, R.A.F., Fibronectin Matrix Depostion and Firbonectin Receptor Expression in Healing and Normal Skin, *J Invest Dermatol*, 94: 128S-134S (1990).

Clarke, D.M., et al., "Improved Post-Thaw Recovery of Peripheral Blood Stem/Progenitor Cells Using a Novel Intracellular-Like Cryopreservation Solution", *Cytotherapy*, 11(4): 472-479 (2009).

Cory, G., "Scratch-Wound Assay", *Methods Mol Biol*, 769: 25-30 (2011).

de Boer, F., et al., "Extensive Early Apoptosis in Frozen-Thawed CD24-positive Stem Cells Decreases Threshold Doses for Haematological Recovery After Autologous Peripheral Blood Progenitor Cell Transplantation", *Bone Marrow Transplantation*, 29: 249-255 (2002).

de Boer, F., et al., "Early Apoptosis Largely Accounts for Functional Impairment of CD34+ Cells in Frozen-Thawed Stem Cell Grafts", *J Hematother Stem Cell Res*, 11(6): 951-963 (2002).

Dominici, M., et al., "Minimal Criteria for Defining Multipotent Mesenchymal Stromal Cells. The International Society for Cellular Therapy Position Statement", *Cytotherapy*, 8(4): 315-317 (2006).

Durand, E.M. and Zon, L.I., "Newley Emerging Roles for Prostaglandin $E_2$ Regulation of Hematopoiesis and Hematopoietic Stem Cell Engraftment", *Current Opinion in Hematology*, 17: 308-312 (2010).

Ehrlich, H.P., et al., "Morphological and Immunochemical Differences Between Keloid and Hypertrophic Scar", *American Journal of Pathology*, 145(1): 105-113 (1994).

Estes, J.M., et al., "Hyaluronate Metabolism Undergoes an Ontogenic Transiton During Fetal Development: Implications for Scar-Free Wound Healing", *J Pediatr Surg*, 28(10): 1227-1231 (1993).

Fan, C.G., et al., "Therpeutic Potentials of Mesenchymal Stem Cells Derived From Human Umbilical Cord", *Stem Cell Rev and Rep*, 7(1): 195-207 (2011).

Fathke, C., et al., "Contribution of Bone Marrow-Derived Cells to Skin: Collagen Depostion and Wound Repair", *Stem Cells*, 22: 812-822 (2004).

Fernandes, K.J.L., et al., "A Dermal Niche for Multipotent Adult Skin-Derived Precursor Cells", *Nature Cell Biology*, 6(11):1082-1093 plus 5 pages of Supplemental Information ( 2004).

Fleming, K.K. and Hubel, A., "Cryopreservation of Hematopoietic Stem Cells: Emerging Science, Technology and Issues", *Transfusion Medicine and Hemotherapy*, 34: 268-275 (2007).

Fong, C.Y., et al., "Comparative Growth Behaviour and Characterization of Stem Cells From Human Wharton's Jelly", *Reproductive BioMedicine Online*, 15(6): 708-718 (2007).

Fong, C.Y., et al., "Derivation Efficiency, Cell Proliferation, Freeze-Thaw Survival, Stem-Cell Properties and Differentiation of Human Warton's Jelly Stem Cells", *Reproductive BioMedicine Online*, 21: 391-401 (2010).

Fong, C.Y., et al., "Human Wharton's Jelly Stem Cells Have Unique Transciptome Profiles Compared to Human Embryonic Stem Cells and Other Mesenchymal Stem Cells", *Stem Cell Rev*, 7(1): 1-16 (2011).

Fong, C.Y., et al., "Human Umbilical Cord Wharton's Jelly Stem Cells and Its Conditioned Medium Support Hematopoietic Stem Cell Expansion Ex Vivo", *J of Cellular Biochemistry*, 113: 658-668 (2012).

Fong, C.Y., et al., "Human Umbilical Cord Wharton's Jelly Stem Cells Undergo Enhanced Chondrogenic Differentiation When Grown on Nanofibrous Scaffolds and in a Sequenctial Two-Stage Culture Medium Environment", *Stem Cell Rev and Rep*, 8: 195-209 (2012).

Fonseka, M., et al., "Human Umbilical Cord Blood-Derived Mesenchymal Stem Cells (hUCB-MSC) Inhibit the Proliferation of K562 (Human Erythromyeloblastoid Leukaemic Cell Line)", *Cell Biol Int*, 36: 793-801 (2012).

Ganta, C., et al., "Rat Umbilical Cord Stem Cells Completely Abolish Rat Mammary Carcinomas With No Evidence of Metastasis or Recurrence 100 Days Post-Tumor Cell Inoculation", *Cancer Res*, 69(5): 1815-1820 (2009).

Garin, M.I., et al., "Ex Vivo Expansion and Charachtersation of CD34+ Cells Derived From Chronic Myeloid Leukaemia Bone Marrow and Peripheral Blood, and From Normal Bone Marrow and Mobilised Peripheral Blood". *Eur J Haematol*, 64(2): 85-92 (2000).

Gauglitz, G.G., et al., Hypertrophic Scarring and Keloids: Pathomechanisms and Current and Emerging Treatment Strategies, *Mol Med*, 17: 113-125 (2011).

Gauglitz, G.G., "Management of Keloids and Hypertrophic Scars: Current and Emerging Options", *Clinical, Cosmetic and Investigational Dermatology*, 6: 103-114 (2013).

Gauthaman, K., et al., "Rock, Inhibitor Y-27632 Increase Thaw-Survival Rates and Preserves Sternness and Differentiation Potential of Human Wharton's Jelly Stem Cells After Cryopreservation", *Stem Cell Rev and Rep*, 6(4): 665-676 (2010).

Guathaman, K., et al., "Osteogenic Differentiation of Human Wharton's Jelly Stem Cells on Nanofibrous Substrates in Vitro", *Tissue Engineering Part A*, 17 (1-2): 71-81 (2011).

Gauthaman, K., et al., "Extra-Embryonic Human Wharton's Jelly Stem Cells Do Not Induce Tumorigenesis, Unlike Human Embryonic Stem Cells", *Reproductive BioMedicine Online*, 24: 235-246 (2012).

Gauthaman, K., et al, "Human Umbilical Cord Wharton's Jelly Stem Cell (hWJSC) Extracts Inhibit Cancer Cell Growth in Vitro", *J Cell Biochem*, 113(6): 2027-2039 (2012).

Gauthaman, K., et al, "Human Wharton's Jelly Stem Cell Conditioned Medium and Cell-Free Lysate Inhibit Human Osteosarcoma and Mammary Carcinoma Cell Growth in Vitro and in Xenograft Mice", *J Cell Biochem*, 114(2): 366-377 (2013).

Gay, A.N., et al., "Wound Healing Characteristics of ICAM-1 Null Mice Devoid of All Isoforms of ICAM-1", *J Surg. Res*, 171(1): e1-e7 (2011).

Gluckman, E., et al., "Outcome of cord-Blood Transplantation From Related and Unrelated Donors", *NEJM*, 337(6): 373-381 (1997).

Gluckman, E., et al., "Cord Blodd Transplantation: State of the Art", *Haematologica*, 94(4): 451-454 (2009).

Hanna, J. and Hubel, A., "Preservation of Stem Cells", *Organogenesis*, 5(3): 134-137 (2009).

Harris, D.T., et al., "Cell-Based Therapy for Epithelial Wounds", *Cytotherapy*, 14(7): 802-810 (2012).

Hoggatt, J., et al., "Prostaglandin E2 Enhances Hematopoietic Stem Cell Homing, Survival, and Proliferation", *Blood*, 113(22): 5444-5455 (2009).

Huang, Y.C., et al., "Umbilical Cord Versus Bone Marrow-Derived Mesenchymal Stromal Cells", *Stem Cells and Development*, 21(15): 2900-2903 (2012).

Iqbal, S.A., et al., "Identification of Fibrocytes From Mesenchymal Stem Cells in Keloid Tissue: A Potential Source of Abnormal Fibroblasts in Keloid Scarring", *Arch Dermatol Res*, 304(8): 665-671 (2012).

Hamann, K.J., et al., "Hyaluronic Acid Enhances Cell Proliferation During Eosinopoiesis Through the CD44 Surface Antigen", *J Immunol*, 154(8): 4073-4080 (1995).

(56) References Cited

OTHER PUBLICATIONS

Hayakawa, J., et al., "5% Dimethyl Sulfoxide (DMSO) and Pentastarch Improves Cryopreservation of Cord Blood Cells Over 10% DMSO", *Transfusion*, 50(10): 2158-2166 (2010).
Heng, B.C., "Effect of Rho-Associated Kinase (ROCK) Inhibitor Y-27632 on the Post-Thaw Viability of Cryopreserved Human Bone Marrow-Derived Mesenchymal Stem Cells", *Tissue Cell*, 41(5): 376-380 (2009).
Jackson, W.M., et al., "Concise Review: Clinical Translation of Wound Healing Therapies Based on Mesenchymal Stem Cells", *Stem Cells Translational Medicine*, 1: 44-50 (2012).
Jäger, R. and Fearnhead, H.O., "'Dead Cells Talking': The Silent Form of Cell Death Is Not So Quiet", *Biochemistry Research International*, Article ID 453838: 8 pages (2012).
Jeon, Y.K., et al., Mesenchymal Stem Cells' Interaction With Skin: Wound—Healing Effect on Fibroblast Cells and Skin Tissue:, *Wound Repair Regen*, 18(6): 655-661 (2010).
Ji, R., et al., "MicroRNA Expression Signature and Antisense-Mediated Depletion Reveal an Essential Role of MicroRNA in Vascular Neointimal Lesion Formation", *Circ Res*, 100: 1579-1588 (2007).
Jin, G., et al., "Stem Cell Differentiation to Epidermal Lineages on Electrospun Nanofibrous Substrates for Skin Tissue Engineering", *Acta Biomater*, 7(8): 3113-3122 (2011).
Jodele, S., et al., "The Contribution of Bone Marrow-Derived Cells to the Tumor Vasculature in Neuroblastoma is Matrix Metalloproteinase-9 Dependent" *Cancer Res*, 65(8): 3200-3208 (2005).
Karahuseyinoglu, S., et al., "Biology of Stem Cells in Human Umbilical Cord Stroma: in Situ and in Vitro Surveys", *Stem Cells*, 25: 319-331 (2007).
Karolina, D.S., et al., "MicroRNA 144 Impairs Insulin Signaling by Inhibiting the Expression of Insulin Receptor Substrate 1 in Type 2 Diabetes Mellitus", *Plos One*, e22839, 6(8): 19 pages (2011).
Kawachi, Y., et al., "Superficial Epithelioma With Sebaceous Differentiation: Immunohistochemical Study of Keratinocyte Differentiation Markers", *Eur J Dermatol*, 21(6): 1016-1017 (2011).
Kieran, I., et al., "Interleukin-10 Reduces Scar Formation in Both Animal and Human Cutaneous Wounds: Results of Two Preclinical and Phase II Randomized Control Studies", *Wound Repair Regen*, 21(3): 428-436 (2013).
Krishnan, A. and Forman, S.J., "Hematopoietic Stem Cell Transplantation for AIDS Related Malignancies", *Curr Opin Oncol*, 22(5): 456-460 (2010).
Kuo, Y.R., et al., "Bone Marrow-Derived Mesenchymal Stem Cells Enhanced Diabetic Wound Healing Through Recruitment of Tissue Regeneration in a Rat Model of Streptozotocin-Induced Diabetes", *Plas Reconstr Surg*, 128: 872-880 (2011).
Kuzuya, H., et al., "Determination of Aloenin, Barbaloin and Isobarbaloin in Aloe Species by Micellar Electrokinetic Chromatography", *J Chromatogr B Biomed Sci Appl*, 572: 91-97 (2001).
LaRocca, G., et al., "Isolation and Characterization of Oct-4+/HLA-G+ Mesenchymal Stem Cells From Human Umbilical Cord Matrix: Differntiation Potential and Detection of New Markers", *Histochem Cell Biol*, 131(2): 267-282 (2009).
Lemoli, R.M., et al., "Interleukin-11 Stimulates the Proliferation of Human Hematopoietic CD34+ and CD34+CD33-DR-Cells and Synergizes With Stem Cell Factor, Interleukin-3, and Granulocyte-Macrophage Colony-Stimulating Factor", *Exp Hematology*, 31: 1668-1672 (1993).
Li, F., et al., "Apoptotic Cells Activate the "Phoenix Rising" Pathway to Promote Wound Healing and Tissue Regeneration", *Sci Signal*, ra 13, 3(110) : 20 pages (2010).
Liang, C.C., et al., "In Vitro Scratch Assay: A Convenient and Inexpensive Method for Analysis of Cell Migration in Vitro", *Nature Protocols*, 2(2): 329-333 (2007).
Liao, B., et al., "MicroRNA Cluster 302-367 Enhances Somatic Cell Reprogramming by Accelerating a Mesenchymal-To-Epithelial Transition", *The Journal of Biological Chemistry*, 286(19): 17359-17364 (2011).
Limaye, L.S. and Kale, V.P., "Cryopreservation of Human Hematopoietic Cells With Membrane Stabilizers and Bioantioxidants as Additives in the Conventional Freezing Medium", *J Hematother Stem Cell Res*, 10(5): 709-718 (2001).
Liu, C., et al., "A Novel PTEN Gene Promoter Mutation and Untypical Cowden Syndrome", *Clin J Cancer Res*, 25(3): 306-311 (2013).
Liu, J., et al., "Suppression of Cholangiocarcinoma Cell Growth by Human Umbilical Cord Mesenchymal Stem Cells: A Possible Rold of Wnt and Akt Signaling", *PlosOne*, 8(4): e62844, 11 pages (2013).
Liu, Y., et al., "Increased Matrix Metalloproteinase-9 Predicts Poor Wound Healing in Diabetic Foot Ulcers", *Diabetes Care*, 32(1): 117-119 (2009).
Lorenz, H.P., et al., "Scarless Wound Repair: A Human Fetal Skin Model", *Development*, 114: 253-259 (1992).
Luo, G., et al., "Promotion of Cutaneous Wound Healing by Local Application of Mesenchymal Stem Cells Derived From Human Umbilical Cord Blood", *Wound Repair Regen*, 18(5): 506-513 (2010).
Ma, K., et al., Effects of Nanofiber/Stem Cell Composite on Wound Healing in Acute Full-Thickness Skin Wounds, *Tissue Eng Part A*, 17(9-10): 1412-1424 (2011).
Ma, Y., et al., "The in Vitro and in Vivo Effects of Human Umbilical Cord Mesenchymal Stem Cells on the Growth of Breast Cancer Cells", *Breast Cancer Res Treat*, 133(2): 473-485 (2012).
Madhyastha, R., et al., "MicroRNA Signature in Diabetic Wound Healing: Promotive Role of miR-21 in Fibroblast Migration", *Int Wound J*, 9(4): 355-361 (2012).
MaHam, A., et al., "Protein-Based Nanomedicine Platforms for Drug Delivery", *Small*, 5(15): 1706-1721 (2009).
Mansilla, E., et al., "Human Mesenchymal Stem Cells are Tolerized by Mice and Improve Skin and Spinal Cord Injuries", *Transplant Proc*, 37(1): 292-294 (2005).
Mareschi, K., et al., "Isolation of Human Mesenchymal Stem Cell: Bone Marrow Versus Umbilical Cord Blood", *Haematologica*, 86: 1099-1100 (2001).
Martin, P., et al., "Wound Healing in the PU.1 Null Mouse-Tissue Repair Is Not Dependent on Inflammatory Cells", *Current Biology*, 13: 1122-1128 (2003).
Maurya, D.K., et al., "Therapy With Un-Engineered Naïve Rat Umbilical Cord Matrix Stem Cells Markedly Inhibits Growth of Muring Lung Adenocarcinoma", *BMC Cancer*, 10: 10 pages (2010).
Maxson, S., et al., "Concise Review: Role of Mesenchymal Stem Cells in Wound Repair", *Stem Cells Translational Medicine*, 1: 142-149 (2012).
Mendonça, F.A.S., et al., "Effects of the Application of Aloe Vera (1.) and Microcurrent on the Healing of Wounds Surgically Induced in Wistar Rats", *Acta Cir Brasileira*, 24(2): 150-155 (2009).
Mogili, N.S., et al., "Altered Angiogenic Balance in Keloids: A Key to Therpeutic Intervetion", *Transl Res*, 159(3): 182-189 (2012).
Moon, J.H., et al., "Isolation and Characterization of Multipotent Human Keloid-Derived Mesenchymal-Like Stem Cells", *Stem Cells Dev*, 17(4): 713-724 (2008).
Moshref, S.S. and Mufti, S.T., "Keloid and Hypertrophic Scars: Comparative Histopathological and Immunohistochemical Study", *JKAU: Med. Sci.*, 17(3): 3-22 (2010).
Muller, M., et al., "Matrix Metalloproteinases and Diabetic Foot Ulcers: The Ratio of MMP-1 to TIMP-1 Is a Predictor of Wound Healing", *Diabetic Med*, 25: 419-426 (2008).
Murphy, G. and Nagase, H., "Progress in Matrix Metalloproteinase Research", *Mol. Aspects Med*, 29(5): 290-308 (2008).
Musina, R.A., et al., "Umbilical Cord Blood Mesenchymal Stem Cells", *Bull Exp Biol Med*, 143(1): 127-131 (2007).
Nagaoka, T., et al., "Delayed Wound Healing in the Absence of Intracellular Adhesion Molecule-1 or L-Selectin Expression", *American Journal of Pathology*, 157(1): 237-247 (2000).
Nekanti, U., et al., "Lone-Term Expansion and Pluripotent Marker Array Analysis of Wharton's Jelly-Derived Mesenchymal Stem Cells", *Stem Cell Dev*, 19(1): 117-130 (2010).
Pappa, K.I. and Anagnou, N.P., "Novel Sources of Fetal Stem Cells: Where Do They Fit on the Developmental Continuum?", *Regen Med*, 4(3): 423-433 (2009).
Pastrana, E., et al., "Eyes Wide Open: A Critical Review of Sphere-Formation as an Assay for Stem Cells", *Cell Stem Cell*, 8(5): 486-498 (2011).

(56) References Cited

OTHER PUBLICATIONS

Pezzolesi, M.G., et al., "Mutation-Positive and Mutation-Negative Patients With Cowden and Bannayan-Riley-Ruvalcaba Syndromes Associated With Distinct 10q Haplotypes", *The American Journal of Human Genetics*, 79: 923-934 (2006).

Prasanna, S.J. and Jahnavi, V.S., "Wharton's Jelly Mesenchymal Stem Cells as Off-The-Shelf Cellular Therapeutics: A Closer Look Into Their Regenerative and Immunomodulatory Properties", *The Open Tissue Engineering and Regenerative Medicine Journal*, 4: 28-38 (2011).

Rachakatla, R.S., et al., "Development of Human Umbilical Cord Matrix Stem Cell-Based Gene Therapy for Experimental Lung Tumors", *Cancer Gene Therapy*, 14: 828-835 (2007).

Rebulla, P., "Cord Blood Banking 2002: 112,010 of 7,914,773 Chances", *Transfusion*, 42(10): 1246-1248 (2002).

Robinson, S.N., et al., "Mesenchymal Stem Cells in Ex Vivo Cord Blood Expansion", *Best Pract Res Clin Haematol*, 24: 83-92 (2011).

Romanov, Y.A., et al., "Searching for Alternative Sources of Postnatal Human Mesenchymal Stem Cells: Candidate MSC-Like Cells From Umbilical Cord", *Stem Cells*, 21: 105-110 (2003).

Rnjak, J., et al., "Severe Burn Injuries and the Role of Elastin in the Design of Dermal Substitutes", *Tissue Eng Part B Rev*, 17(2): 81-91 (2011).

Salama, H., et al., "Autologuous Hematopoietic Stem Cell Transplantation in 48 Patients With End-Stage Chronic Liver Disease", *Cell Transplantation*, 16: 1475-1486 (2010).

Sarugaser, R., et al., "Human Umbilical Cord Perivascular (HUCPV) Cells: A Source of Mesenchymal Progenitors", *Stem Cells* 23: 220-229 (2005).

Sasaki, M., et al., "Mesenchymal Stem Cells are Recruited Into Wounded Skin and Contribute to Wound Repair by Transdifferentiation Into Multiple Skin Cell Type", *The Journal of Immunology*, 180: 2581-2587 (2008).

Sasnoor, L.M., et al., "Supplementation of Conventional Freezing Medium With a Combination of Catalase and Trehalose Results in Better Protection of Surface Molecules and Functionality of Hematopoietic Cells", *J Hematother Stem Cell Res*, 12:553-564 (2003).

Sasnoor, L.M., et al., "A Combination of Catalase and Trehalose as Additives to Conventional Freezing Medium Results in Improved Cryoprotection of Human Hematopoietic Cells With Reference to in Vitro Migration and Adhesion Properties", *Transfusion*, 45(4): 622-633 (2005).

Sasnoor, L.M., et al., "Prevention of Apoptosis as a Possible Mechanism Behind Improved Cryoprotection of Hematopoietic Cells by Catalase and Trehalose", *Transplantation*, 80: 1251-1260 (2005).

Schneider, R.K., et al., "Long-Term Survival and Characterisation of Human Umbilical Cord-Derived Mesenchymal Stem Cells on Dermal Equivalents", *Differentiation*, 79(3): 182-193 (2010).

Seshareddy, K., et al., "Method to Isolate Mesenchymal-Like Cells From Wharton's Jelly of Umbilical Cord", *Method Cell Biol*, 86: 101-119 (2008).

Shaw, T.J. and Martin, P., "Wound Repair At a Glance", *Journal of Cell Science*, 122(18): 3209-3213 (2009).

Shilo, S., et al., "Cutaneous Wound Healing After Treatment With Plant-Derived Human Recombinant Collagen Flowable Gel", *Tiss Eng Part A*, 19(13-14): 1519-1526 (2013).

Shin, L. and Peterseon, D.A., "Human Mesenchymal Stem Cell Grafts Enhance Normal and Impaired Wound Healing by Recruiting Existing Endogenous Tissue Stem/Progenitor Cells", *Stem Cells Translational Medicine*, 2: 33-42 (2013).

Spaeth, E.L., et al., "Mesenchymal Stem Cell Transition to Tumor-Associated Fibroblasts Contributes to Fibrovascular Network Expansion and Tumor Progression", *PlosOne*, 4(4): e4992: 11 pages (2009).

Stevens, L.J. and Page-McCaw, A., "A Secreted MMP Is Required for Reepithelialization During Wound Healing", *Molecular Biology of the Cell*, 23: 1068-1079 (2012).

Stoff, A., et al., "Promotion of Incisional Wound Repair by Human Mesenchymal Stem Cell Transplantation", *Exp. Dermatol*, 18(4): 362-369 (2009).

Stroh, C., et al., "The Role of Caspases in Cryoinjury: Caspase Inhibition Strongly Improves the Recovery of Cryopreserved Hematopoietic and Other Cells", *The FASEB Journal*, 16: 1651-1653 (2002).

Suárez, Y., et al., "Dicer-Dependent Endothelial MicroRNAs Are Necessary for Postnatal Angiogenesis", *PNAS*, 105(37): 14082-14087 (2008).

Subramanian, A., et al.,"Human Umbilical Cord Wharton's Jelly Mesenchymal Stem Cells Do Not Transform to Tumor-Associated Fibroblasts in the Presence of Breast and Ovarian Cancer Cells Unlike Bone Marrow Mesenchymal Stem Cells", *J Cell Biochem*, 113(6): 1886-1895 (2012).

Sudo, K., et al., "Mesenchymal Progenitors Able to Differentiate Into Osteogenic, Chondrogenic, and/or Adipogenic Cells in Vitro Are Present in Most Primary Fibroblast-Like Cell Populations", *Stem Cells*, 25: 1610-1617 (2007).

Sullivan, S.R., et al., "Validation of a Model for the Study of Multiple Wounds in the Diabetic Mouse (db/db)", *Plast Reconstr Surg*, 113(3): 953-960 (2004).

Sun, B., et al., "Human Umbilical Cord Blood Mesenchymal Stem Cell-Derived Extracellular Matrix Prohibits Metastic Cancer Cell MDA-MB-231 Proliferation", *Cancer Lett*, 196(2): 178-185 (2010).

Szulgit, G., et al., "Alterations in Fibroblast $\alpha1\beta1$ Integrin Collagen Receptor Expression in Keloids and Hypertrophic Scars", *Journal of Investigative Dermatology*, 118: 409-415 (2002).

Takzare, N., et al., "Influence of Aloe Vera Gel on Dermal Wound Healing Process in Rat", *Toxicology Mechanisms and Methods*, 19: 73-77 (2009).

Taghizadeh, R.R., et al., "Wharton's Jelly Stem Cells: Future Clinical Applications", *Placenta*, 32: S311-S315 (2011).

Tocco, I., et al., "Nanotechnology-Based Therapies for Skin Wound Regeneration", *Journal of Nanomaterials*, Article ID 714134: 11 Pages (2012).

Toma, J.G., et al., "Isolation of Multipotent Adult Stem Cells From the Dermis of Mammalian Skin", *Nature Cell Biology*, 3: 778-784 (2001).

Toma, J.G., et al., "Isolation and characterization of Multipotent Skin-Derived Precursors From Human Skin", *Stem Cells*, 23: 727-737 (2005).

Troyer, D.L. and Weiss, M.L., "Concise Review: Wharton's Jelly-Derived Cells Are a Primitive Stromal Cell Population", *Stem Cells*, 26: 591-599 (2008).

Vazquez, B., et al., "Antiinflammatory Activity of Extracts From Aloe Vera Gel", *J Ethnopharmacol*, 55: 69-75 (1996).

Walter, M.N., et al., "Mesenchymal Stem Cell-Conditioned Medium Accelerates Skin Wound Healing: An Invitro Study of Fibroblast and Keratinocyte Scratch Assays", *Exp Cell Res*, 316(7): 1271-1281 (2010).

Wang, H.S., et al., "Mesenchymal Stem Cells in the Wharton's Jelly of the Human Umbilical Cord", *Stem Cells*, 22: 1330-1337 (2004).

Wang, X.Y., et al., "Identificatin of Mesenchymal Stem Cells in Aorta-Gonad-Mesonephros and Yolk Sac of Human Embryos", *Blood*, 111(4): 2436-2443 (2008).

Wang, Y., et al., "A Toxicity Study of Multiple-Administration Human Umbilical Cord Mesenchymal Stem Cells in Cynomolgus Monkeys", *Stem Cells and Development*, 21(9): 1401-1408 (2012).

Weiss, M.L., et al., "Human Umbilical Cord Matrix Stem Cells: Preliminary Characterization and Effect of Transplantation in a Rodent Model of Parkinson's Disease", *Stem Cells*, 24: 781-792 (2006).

Weiss, M.L., et al., "Immune Properties of Human Umbilical Cord Wharton's Jelly-Derived Cells", *Stem Cells*, 26:2865-2874 (2008).

Welch, W.J., et al., "Response of Mammalian Cells to Metabolic Stress; Changes in Cell Physiology and Structure/Function of Stress Proteins", *Curr Top Hicrobiol Immunol*, 167: 31-55 (1991).

Wels, J., et al., "Migratory Neighbors and Distant Invaders: Tumor-Associated Niche Cells", *Genes & Development*, 22:559-574 (2008).

(56) References Cited

OTHER PUBLICATIONS

Wexler, S.A., et al., "Adult Bone Marrow Is a Rich Source of Human Mesenchymal Stem Cells But Umbilical Cord and Mobilized Adult Blood Are Not", *British Journal of Haematology*, 121: 368-374 (2003).

White-Chu, E.F., et al., "Pressure Ulcers in Long-Term Care", *Clin Geriatr Med*, 17(2): 241-258 (2011).

Wu, S., et al., "Microvesicles Derived From Human Umbilical Cord Wharton's Jelly Mesenchymal Stem Cells Attenuate Bladder Tumor Cell Growth in Vitro and in Vivo", *PlosOne*, 8(4): e61366: 12 pages (2013).

Wu, Y., et al., "Mesenchymal Stem Cells Enhance Wound Healing Through Differentiation and Angiogenesis", *Stem Cells*, 25: 2648-2659 (2007).

Yang, F., et al., "Genetic Engineering of Human Stem Cells for Enhanced Angiogenesis Using Biodegradable Polymeric Nanoparticles", *PNAS*, 107(8): 3317-3322 (2010).

Yew, T.L., et al., "Enhancement of Wound Healing by Human Multipotent Stromal Cell Conditioned Medium: The Paracrine Factors and p38 MAPK Activation", *Cell Transplantation*, 20: 693-706 (2011).

Yukami, T., et al., "Endothelial Selectins Regulate Skin Wound Healing in Cooperation With L-Selectin and ICAM-1", *Journal of Leukocyte Biology*, 82:519-531 (2007).

Zhang, K., et al., "Increased Types I and III Collagen and Transforming Growth Factor-β1 mRNA and Protein in Hypertrophic Burn Scar", *J Invest Dermatol*, 104: 750-754 (1995).

Zhang, Q., et al., "Tumor-Like Stem Cells Derived From Human Keloid Are Governed by the Inflammatory Niche Driven by IL-17/IL-6 Axis", *PlosOne*, 4(11): e7798: 16 pages (2009).

Zhang, Y., et al., "Co-Culture of Umbilical Cord Blood CD34+ Cells With Human Mesenchymal Stem Cells", Tissue Engineering, 12(8): 2161-2170 (2006).

Zhang, Y.Z., et al., "Biomimetic and Bioactive Nanofibruous Scaffolds From Electrospun Composite Nanofibers", *International Journal of Nanomedicine*, 2(4): 623-638 (2007).

Office Communication, U.S. Appl. No. 13/667,370 entitled "Wharton's Jelly Mesenchymal Stem Cells and Uses Thereof", filed Nov. 2, 2012, Date of Communication: May 14, 2015.

Irvine et al., "Human Umbilical Cord Conditioned Medium: a Stimulus for Human CFUf-G", Exp. Hematol., vol. 12, No. 1, pp. 19-24, 1984.

Venugopal et al., "Isolation. characterization, and gene expression analyusis of Wharton's jelly-derived mesenchymal stem cells under xeno-free culture conditions", Stem Cells and Cloning: Advances and Applications 4 39-50, 2011.

Azari, O., et al., "Effects of Transplanted Mesenchymal Stem Cells Isolated from Wharton's Jelly of Caprine Umbilical Cord on Cutaneous Wound Healing; Histopathological Evaluation", Vet Res Commun, 35(4): 211-222 (2011).

Cabrera, C., et al., "The Role of Biologically Active Peptides in Tissue Repair Using Umbilical Cord Mesenchymal Stem Cells", Ann N Y Acad Sci., 1270: 93-97 (2012).

Kim, J.Y., et al., "Human Cord Blood-Derived Endothelial Progenitor Cells and Their Conditioned Media Exhibit Therapeutic Equivalence for Diabetic Wound Healing", Cell Transplantation, 19: 1635-1644 (2010).

Magin, A.S., et al., "Primary Cells as Feeder Cells for Coculture Expansion of Human Hematopoietic Stem Cells from Umiblical Cord Blood—A Comparative Study", Stem Cells and Development, 18:173-186 (2009).

Shohara, R., et al., "Mesenchymal Stromal Cells of Human Umbilical Cord Wharton's Jelly Accelerate Wound Healing by Paracrine Mechanisms", Cytotherapy, 14(10): 1171-1181 (2012).

Applicant Initiated Interview Summary for U.S. Appl. No. 13/667,370, "Wharton's Jelly Mesenchymal Stem Cells and Uses Thereof"; date of mailing Feb. 26, 2015.

Advisory Action for U.S. Appl. No. 13/667,370, "Wharton's Jelly Mesenchymal Stem Cells and Uses Thereof"; date of mailing Feb. 5, 2015.

Office Action made Final for U.S. Appl. No. 13/667,370, "Wharton's Jelly Mesenchymal Stem Cells and Uses Thereof"; date of mailing Oct. 21, 2014.

Non-Final Office Action for U.S. Appl. No. 13/667,370, "Wharton's Jelly Mesenchymal Stem Cells and Uses Thereof"; date of mailing Mar. 13, 2014.

International Search Report and the Written Opnion of the International Searching Authority for International Patent Application No. PCT/SG2013/000348, "Wound Dressing Nanomesh Impregnated with Human Umbilical Cord Wharton's Jelly Stem Cells", date of mailing Oct. 22, 2013.

Notification Concerning Transmittal of International Preliminary Report on Patentability for International Patent Application No. PCT/SG2013/000348, "Wound Dressing Nanomesh Impregnated with Human Umbilical Cord Wharton's Jelly Stem Cells", date of mailing Oct. 22, 2013.

\* cited by examiner

Figure 7

Experimental Design

| Composition of Control Freezing Medium | Composition of hWJSC-CM Freezing Medium |
|---|---|
| StemSpan SFEM Basal Medium<br>2mM L-Glutamine and<br>1% Antibiotic/Antimyotic<br>40% of 25% human serum albumin<br>10% DMSO | 24hrs hWJSC-CM in StemSpan SFEM medium<br>2mM L-Glutamine and<br>1% Antibiotic/Antimyotic<br>40% of 25% human serum albumin<br>10% DMSO |
| Composition of Control Post-Thaw Medium | Composition of hWJSC-CM Post-Thaw Medium |
| StemSpan SFEM Basal Medium<br>2mM L-Glutamine and<br>1% Antibiotic/Antimyotic<br>40% FBS | 24hrs hWJSC-CM in StemSpan SFEM medium<br>2mM L-Glutamine and<br>1% Antibiotic/Antimyotic<br>40% FBS |

METHODS OF FREEZING STEM CELLS

RELATED APPLICATION

This application claims the benefit of U.S. Provisional Application No. 61/721,398, filed on Nov. 1, 2012. The entire teachings of the above application are incorporated herein by reference.

BACKGROUND OF THE INVENTION

Stem cells hold tremendous promise for the treatment of various incurable diseases by transplantation therapy. Of the various stem cell types, hematopoietic stem cell (HSC) transplantation has been the most successful in the clinic. Since the introduction of bone marrow HSC transplantation in 1968, HSCs have been used in the treatment of hematopoietic diseases such as leukemia, lymphoma, thalassemia and autoimmune disorders. HSC transplantation has also been shown to produce promising results for the treatment of chronic liver failure and acquired immunodeficiency syndrome.

HSCs are obtained from many different sources such as bone marrow (BM), peripheral blood (PB) and umbilical cord blood (UCB). HSCs isolated from the UCB have several advantages for transplantation therapy compared to the BM and PB. They are easily collected and stored in cord blood banks, have lesser risk of graft versus host disease (GVHD) in transplant recipients due to their immune naivety and require less stringent criteria for donor-recipient matching. Additionally they have high proliferation rates, autocrine production of hematopoietic factors and longer telomere lengths due to their younger chronological age.

However, a major limitation to their use in transplantation is the low cell numbers in a single UCB unit. The yield of HSCs from a single freeze-thawed UCB unit is typically about $1.0 \times 10^7$ cells. This number is far less than the recommended cell numbers required for transplantation. Recommended cell numbers range from $2.5\text{-}5 \times 10^6$ CD34+ cells/kg for a successful engraftment. As such, single unit UCB-derived HSC transplantation is often a challenge for the treatment of adults.

Thus, a need to increase stem cell numbers UCB units (e.g., a single UCB unit) is needed.

SUMMARY OF THE INVENTION

In some aspects, the invention is directed to a method of freezing stem cells. The method comprises introducing the stem cells into a cell culture medium that has been conditioned with Wharton's Jelly mesenchymal stem cells (WJSCs), thereby producing a stem cell culture and slowly freezing the stem cell culture, thereby freezing the stem cells.

In other aspects, the invention is directed to compositions comprising stem cells produced by the methods provided herein. In yet other aspects, the invention is directed to pharmaceutical compositions comprising the stem cells produced by the methods provided herein.

BRIEF DESCRIPTION OF THE DRAWINGS

The foregoing will be apparent from the following more particular description of example embodiments of the invention, as illustrated in the accompanying drawings in which like reference characters refer to the same parts throughout the different views. The drawings are not necessarily to scale, emphasis instead being placed upon illustrating embodiments of the present invention.

FIG. 7 is a schematic of the compositions used in Example 2.

DETAILED DESCRIPTION OF THE INVENTION

Figures 1A, 1B, 1C, 1D, 1E, 1F:
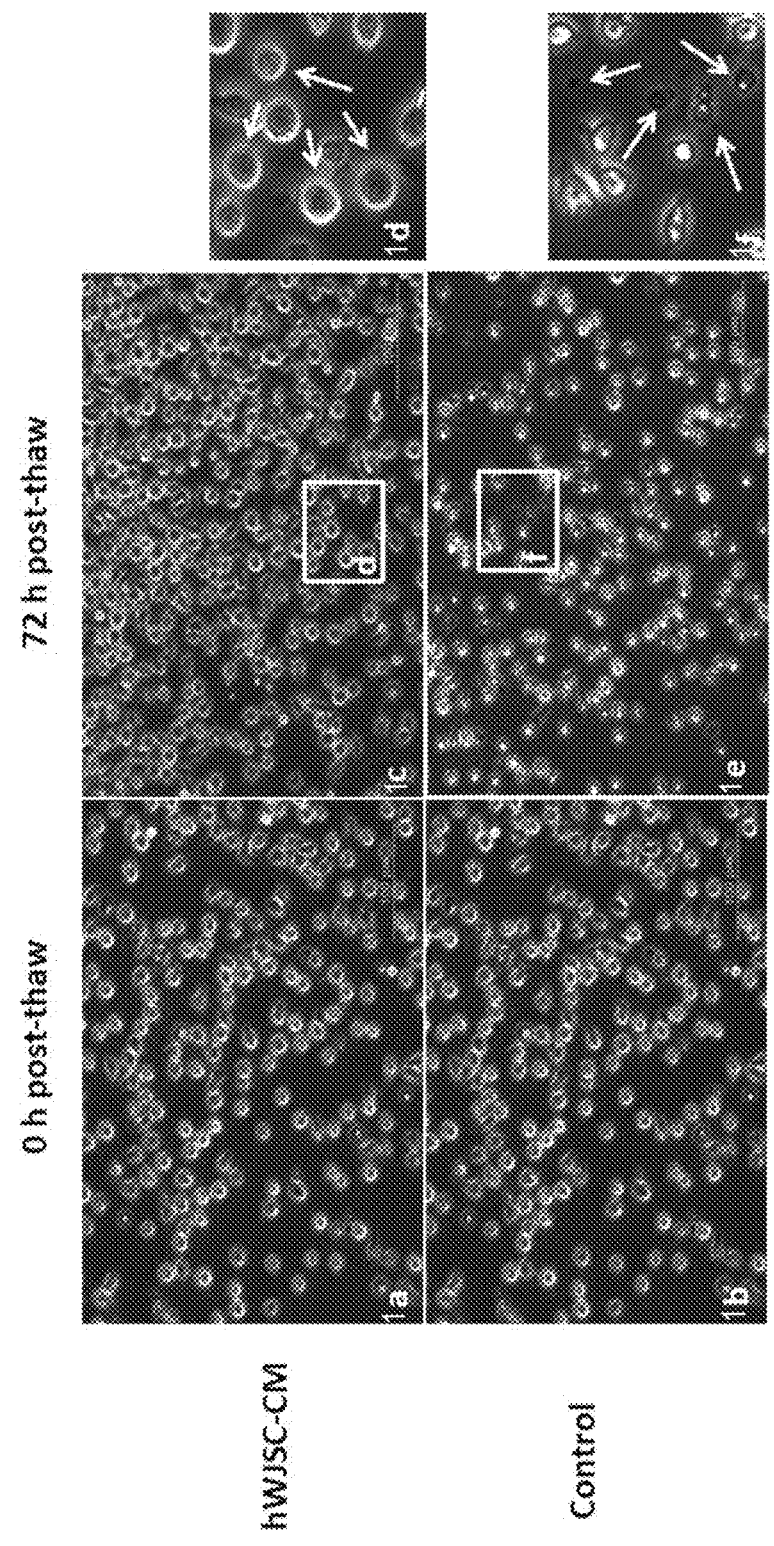
FIGS. 1A-1F: 1A, 1B: Morphology of CD34+ cells frozen in hWJSC-CM, thawed and analysed immediately (0 h post-thaw). Note the thawed CD34+ cells that were frozen in hWJSC-CM having similar healthy circular morphology as controls. 1C-1F: Morphology of CD34+ cells frozen in hWJSC-CM, thawed and then grown in hWJSC-CM for 72 h (72 h post-thaw). (1C, 1D): Note low and high magnification of healthy CD34+ cells (arrows) (1E, 1F): Controls showing greater cell death (cell debris) (arrows). Scale bar: 100 μm.

A description of example embodiments of the invention follows.

Hematopoietic stem cells (HSCs) from umbilical cord blood have been successfully used to treat blood disorders but one major hurdle is the relatively low cell dose available. Double cord blood unit transplantation results in elevated engraftment failure because one unit predominates over the other. Various approaches are thus being undertaken to expand HSCs ex vivo from single cord blood units. Reported herein is a protocol involving slow freezing (e.g., −1° C. per minute to −120° C.)+freezing medium that enhances thaw-survival of stem cells (e.g., CD34+ cells). Post-thawing, the fold, percentage and colony forming unit numbers of CD34+ cells were significantly increased (2.08±0.3; 102±1.17%; 1.07±0.02 respectively) while the percentages of apoptotic, necrotic, dead and sub-G1 phase cells (91.06±3.63%; 91.80±5.01%; 95.6±3.61%; 86.1±16.26% respectively) were significantly decreased compared to controls. Post-thaw culture (e.g., in 24 h-50% hWJSC-CM+FBS for 72 h) showed further significant increases in CD34+ cells (fold: 2.28±0.17; percentage: 153.3±21.99%, CFU: 1.6±0.19) and significant decreases in apoptotic, necrotic, dead and sub-G1 cells (49.2±3.59%; 62.0±4.30%; 56.6±5.06%; 28.6±5.74% respectively) compared to controls. These improvements are likely related to the high levels of cytokines, cell adhesion molecules and growth factors in hWJSC-CM that help to preserve cell membrane integrity during freezing and stimulate mitosis post-thaw.

Accordingly, in one aspect the invention is directed to a method of freezing stem cells. The method comprises introducing the stem cells into a (one or more) cell culture medium that has been conditioned with Wharton's Jelly mesenchymal stem cells (WJSCs), thereby producing a stem cell culture and slowly freezing the stem cell culture, thereby freezing the stem cells. In a particular aspect, the stem cells are hematopoietic stem cells (HSCs). In yet another aspect, the stem cells are human HSCs (hHSCs). The methods have been exemplified using HSCs and for purposes of convenience the methods will be discussed with particular reference to HSCs. However, those of skill in the art will appreciate that the methods described herein can be performed with a variety of stem cells.

As used herein, HSCs (e.g., human HSCs) are self-renewing stem cells that, when engrafted into a recipient, can "repopulate" or "reconstitute" the hematopoietic system of a graft recipient (e.g., a human; a non-human mammal; an immunodeficient mammal) and sustain (e.g., long term) hematopoiesis in the recipient. HSCs are unipotent stem cells that give rise to (differentiate into) blood cell types including myeloid (e.g., monocytes and macrophages, neutrophils, basophils, eosinophils, erythrocytes, megakaryocytes/platelets, dendritic cells) and lymphoid lineages (e.g., T-cells, B-cells, NK-cells). HSCs express the cell marker CD34 and are commonly referred to as "CD34+". As understood by those of skill in the art, HSCs can also express other cell markers, such as CD133 and/or CD90 ("CD133+", "CD90+").

HSCs are found in bone marrow such as in femurs, hip, ribs, sternum, and other bones of a donor (e.g., vertebrate animals such as mammals, including humans, primates, pigs, mice, etc.). Other sources of HSCs for clinical and scientific use include umbilical cord blood, placenta, fetal liver, peripheral blood (e.g., mobilized peripheral blood, non-mobilized (or unmobilized) peripheral blood), fetal spleen, embryonic stem cells, and aorta-gonad-mesonephros (AGM), or a combination thereof.

As known in the art, HSCs can be obtained from these sources using a variety of methods known in the art. For example, HSCs can be obtained directly by removal from the bone marrow, e.g., in the hip, femur, etc., using a needle and syringe, or from blood such as cord blood, blood from placenta (e.g., following pre-treatment of the donor with e.g., cytokines, such as granulocyte colony-stimulating factor (G-CSF), that induce cells to be released from the bone marrow compartment) or combination thereof.

As described herein, the method comprises introducing the stem cells into a (one or more) cell culture medium that has been conditioned with Wharton's Jelly mesenchymal stem cells (WJSCs), also referred to herein as WJSC condition medium (WJSCCM; WJSC-CM). In one aspect, the stem cells are cultured with a composition comprising, consisting essentially of or consisting of WJSC conditioned medium (e.g., allogeneic and/or autologous). "Wharton's jelly" refers to a mucilaginous jelly-like substance that occurs in the umbilical cord. Large numbers of bona fide, fully characterized mesenchymal stem cells (MSCs) with high proliferation rates and low population doubling times have been reported in the human umbilical cord Wharton's Jelly (referred to herein as "WJSCs" or "hWJSCs") by several workers. In some aspects, it has been shown that about $4.6 \times 10^6$ fresh live hWJSCs can be harvested from about 1 cm of umbilical cord and the stemness properties of these hWJSCs lasted longer than bone marrow MSCs in vitro (10 vs 3 passages). hWJSCs were also shown to be hypoimmunogenic, thus allowing their use in both autologous and allogeneic settings without the concerns of graft versus host disease, and thaw survival rates of hWJSCs after cryopreservation were greater than 90%.

As described herein, a variety of methods for obtaining WJSCs from umbilical cord are known in the art (e.g., Weiss et al., Stem Cells, 24:781-792 (2006), Fong et al., Reprod Biomed Online, 15:708-718 (2007), Fong e al., Reprod Biomed Online, 21:391-401 (2010), Wang et al., Stem Cells, 22:1330-1337 (2004), Romanov et al., Stem Cells, 21:105-110 (2003), Sarugaser et al., Stem Cells, 23:220-229 (2005), Karahuseyinoglu et al., Stem Cells, 25:319-331 (2007), all of which are incorporated herein by reference). For example, as exemplified herein WJSCs can be obtained from one or more pieces of umbilical cord that have been slit open and inverted onto a Petri dish containing an enzymatic solution and incubated at 37° C. in a 5% $CO_2$ in air atmosphere for 45 minutes to allow loosening and separation of the Wharton's jelly from the umbilical cord. The separated Wharton's jelly can then be syringed through an 18G needle to further break up, and release the WJSCs from, the Wharton's jelly.

The stem cells and/or WJSCs for use in the methods can be obtained from a single donor or multiple donors. In addition, the stem cells (e.g., HSCs) and/or WJSCs used in the methods described herein can be freshly isolated, frozen (e.g., cryopreserved), or a combination thereof.

Typically, the HSCs and/or WJSCs are of mammalian origin. As used herein, the terms "mammal" and "mammalian" refer to any vertebrate animal, including monotremes, marsupials and placental, that suckle their young and either give birth to living young (eutharian or placental mammals) or are egg-laying (metatharian or nonplacental mammals). Examples of mammals include primates (e.g., human, monkeys, chimpanzees), rodents (e.g., rats, mice, guinea pigs), canines, felines, and ruminants (e.g., cows, pigs, horses). In one aspect, the stem cells are human HSCs (hHSCs). In another aspect, the WJSCs are human WJSCs (hWJSCs).

The stem cells and/or WJSCs for use in the methods provided herein can be isolated, pure, or substantially pure. As used herein, "isolated" (e.g., isolated HSCs; isolated WJSCs) refers to substantially isolated with respect to the complex (e.g., cellular) milieu in which it occurs such as isolated from an organ, body, tissue, blood, or culture medium. In some instances, the isolated material will form part of a composition (for example, a crude extract containing other substances), buffer system, culture system or reagent mix. In other circumstances, the material can be purified to essential homogeneity. For example, an isolated composition of stem cells or WJSCs can comprise at least about 50%, at least about 55%, at least about 60%, at least about 65%, at least about 70%, at least about 75%, at least about 80%, at least about 85%, at least about 90%, at least about 95%, or at least about 99% (on a total cell number basis) of all cells present.

In one aspect of the invention, the stem cells and the WJSCs are obtained from different sources (e.g., individuals, such as from the umbilical cords of different individuals). In other aspects of the invention, the stem cells and WJSCs are obtained from a similar (e.g., different individuals such as from the umbilical cords of different individuals of the same species) or the same source (e.g., the same individual such as from the umbilical cord of a single individual). In a particular aspect, the WJSCCM is conditioned with WJSCs that are obtained from the same source as the stem cells.

Thus, for example, in one aspect, the stem cells, the WJSCs and/or the WJSCCM are obtained from different individuals (e.g., syngeneic, xenogeneic). In particular aspects, the stem cells, the WJSCs and/or the WJSCCM are obtained from different individuals of the same species (e.g., allogeneic). In yet other aspects, the stem cells, the WJSCs and/or the WJSCCM are obtained from the same individual (e.g., autologous).

In the methods provided herein the cells are cultured in a (one or more) culture medium during one or more steps of the method. In some aspects, the culture medium is a culture medium for growth, freezing (freezing medium), expansion (expansion medium), thawing (thawing medium), post-thaw medium and the like. As used herein, a medium or cell culture medium is a preparation made specifically for the growth, storage, or transport of cells. The variety of media that exist allow for the culturing of cells in general (e.g., basal medium) or specific cell types (e.g., differential media, selective media, test media, and defined media). The medium can be in a liquid or solid form. In one aspect, solid medium is a liquid medium that has been solidified with an agent such as AGAR or GELATIN. As will be appreciated by those of skill in the art, cell culture media can be prepared using routine skills or obtained from a variety of commercial sources (Fong e al., Reprod Biomed Online, 21:391-401 (2010)).

As used herein, a "basal medium" is typically an unsupplemented medium which promotes the growth of many types of cells which do not require any special nutrient supplements for growth (e.g., Eagle's minimal essential medium (EMEM); Dulbecco's modified Eagle's medium (DMEM)). As will be appreciated by those of skill in the art, a basal medium can comprises a variety of components such as one or more amino acids (e.g., non-essential amino acids, essential amino acids), salts (e.g., calcium chloride, potassium chloride, magnesium sulfate, sodium chloride, and monosodium phosphate), sugars (e.g., glucose), and vitamins (e.g., folic acid, nicotinamide, riboflavin, B12), iron and pH indicators (e.g., phenol red). The basal medium can further comprise proteins (e.g., albumin), hormones (e.g., insulin), glycoproteins (e.g., transferrin), minerals (e.g., selenium), serum (e.g., fetal bovine serum), antibiotics, antimycotics and glycosaminoglycans.

As used herein, an "enriched medium" is a cell culture medium to which has been added one or more additives or supplements to enhance the growth of one or more particular cell types. Examples of additive that enhance cell growth include cytokines (e.g., interleukins such as IL-1a, IL-6, IL-7, IL-8), stem cell factors (e.g., SCF), cell adhesion molecules (e.g., inter-cellular adhesion molecule 1 (ICAM-1)), growth factors (e.g., hepatic growth factor), hyaluronic acid, hormones (e.g., insulin), glycoproteins (e.g., transferrin), minerals (e.g., selenium), serum (e.g., fetal bovine serum) and glycosaminoglycans.

As used herein "conditioned medium" is a cell culture media containing biologically active components obtained from cells or tissues that are or were cultured in the medium and have released into the media substances affecting certain cell functions (e.g., growth, lysis). The conditioned medium can, but typically does not, contain the cells that were previously cultured in the medium.

As used herein "basal conditioned medium" is an unsupplemented cell culture medium that has already been used (e.g., partially) to culture cells. Although depleted of some components, it is enriched with cell derived material (e.g., secreted), probably including small amounts of growth factors. In some cases, such cell conditioned medium can, for example, support the growth of cells at much lower density and, can be mixed with some fresh medium.

As used herein an "enriched conditioned medium" is a cell culture medium that has been used (e.g., partially) to culture cells and further comprises additives that enhance cell growth. Examples of additive that enhance cell growth include cytokines (e.g., interleukins such as IL-1a, IL-6, IL-7, IL-8), stem cell factors (e.g., SCF), cell adhesion molecules (e.g., inter-cellular adhesion molecule 1 (ICAM-1)), growth factors (e.g., hepatic growth factor; fibroblast growth factor), hyaluronic acid, and glycosaminoglycans.

In particular aspects, the conditioned medium is a cell culture medium (e.g., basal; enhriched) that has been conditioned with WJSCs, referred to herein as Wharton's jelly stem cell conditioned medium (WJSCCM). In a particular aspect, the WJSCCM is human WJSCCM (hWJSCCM) in which the cell culture medium has been conditioned with human WJSCs.

Thus, WJSCCM is conditioned medium that has been previously used to culture WJSCs and typically, but not necessarily, does not include the WJSCs. As will be appreciated by those of skill in the art, various concentrations of conditioned medium can be used in the methods. For example, in the methods described herein, about 40%, 50%, 60%, 70%, 80%, 90% or 100% volume/volume (v/v) conditioned medium diluted in, for example, BM and/or EM, can be used. In one aspect, the medium previously used to culture the WJSCs is a basal medium. In another aspect, the medium previously used to culture WJSCs is a conditioned medium. In yet another aspect, the medium previously used to culture WJSCs is an enriched medium. In yet another aspect, the cell culture medium is hWJSCCM which is cell culture medium that has been conditioned with hWJSCs.

In particular aspects, the cell culture medium can be conditioned with WJSCs for about 2 hours (h), 4 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 48 hours, 50 hours, 52 hours, 54 hours, 56 hours, 58 hours, 60 hours, 62 hours, 64 hours, 66 hours, 68 hours, 70 hours, 72 hours, 74 hours, 76 hours, 78 hours, 80 hours, 82 hours, 84 hours, 86 hours, 88 hours, 90 hours, 92 hours, 94 hours or 96 hours, etc.

In other aspects, the concentration of the cell culture medium for use in the methods is about 5% v/v, 10% v/v, 15% v/v, 20% v/v, 25% v/v, 30% v/v, 35% v/v, 40% v/v, 45% v/v, 50% v/v, 55% v/v, 60% v/v, 65% v/v, 70% v/v, 75% v/v, 80% v/v, 85% v/v, 90% v/v, 95% v/v or 100% v/v.

In a particular aspect, the method is performed using a 24 h-50% v/v hJWSC-CM to freeze stem cells.

In other aspects, the cell culture medium in which the stem cells are frozen can further comprises one or more cryoprotectants, cell culture supplements, amino acids, antibiotics, antimyotics or combinations thereof. Examples of cryoprotectants include dimethyl sulfoxide (DMSO), glycerol, ethylene glycol and the like, and/or combinations thereof.

Examples of cell culture supplements includes serum (e.g., human serum, bovine serum, fetal bovine serum (FBS)), serum replacement, components thereof such as albumin (e.g. recombinant; fraction V) and the like and/or combinations thereof. In other aspects, the culture medium is serum free.

Examples of amino acids include alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, valine or variants and/or combinations thereof.

Examples of antibiotics include penicillin, streptomycin, gentamycin and the like and/or combinations thereof. Examples of antimyotics include amphotericin B and the like and/or combinations thereof.

As will be appreciated by those of skill in the art, the cell culture medium can further comprise about 0.5%, 1%, 5%, 10%, 15%, 20%, 25%, 30%, 35%, 40%, 45%, 50%, 55%, 60%, 65%, 70%, 75%, 80%, 85%, 90%, 95%, or 99% cryoprotectants, cell culture supplements, amino acids, antibiotics, antimyotics or combinations thereof.

In a particular aspect, the freezing medium comprises DMSO+FBS+24 h-50% hWJSC-CM. In yet another aspect, the freezing medium comprises DMSO+ human serum albumin+24 h-50% hWJSC-CM.

In some aspects, the components of a (one or more) culture medium is isogeneic, syngeneic, allogeneic or xenogeneic. In other aspects, the culture medium used in the methods lacks components derived from an organism other than the organism from which the stem cell are derived (e.g., xeno-free). For example, provided herein is a method of freezing human stem cells wherein the method comprises introducing the human stem cells (human HSCs) into a culture medium that lacks non-human components or lacks components obtained from another species (e.g., the culture medium lacks bovine serum), thereby producing a stem cell culture and slowly freezing the stem cell culture. In a particular aspect, the method comprises freezing human stem cells (e.g., human umbilical cord blood CD34+ cells) using a culture medium comprising human serum (e.g., human serum albumin).

As described herein the stem cells are frozen slowly. In particular aspect, the stem cells are slowly frozen to about $-100°$ C., $-110°$ C., $-120°$ C., $-130°$ C., $-140°$ C. or $-150°$ C. In other aspects, the stem cells are slowly frozen using a freezing rate of about (slowly frozen by lowering the temperature of the stem cell culture at about) $-0.5°$ C. per minute, $-1°$ C. per minute, $-1.5°$ C. per minute, $-2°$ C. per minute, $-2.5°$ C. per minute, $-3°$ C. per minute, $-3.5°$ C. per minute, $-4°$ C. per minute, $-4.5°$ C. per minute or $-5°$ C. per minute, $-5.5°$ C. per minute, $-6°$ C. per minute, $-6.5°$ C. per minute, $-7°$ C. per minute, $-7.5°$ C. per minute, $-8°$ C. per minute, $-8.5°$ C. per minute, $-9°$ C. per minute, $-9.5°$ C. per minute, or $-10°$ C. per minute.

As will be appreciated by those of skill in the art, the methods described herein can further comprise storing the stem cells. For example, the stem cells can be stored in a liquid phase of nitrogen or in a vapor phase of nitrogen.

As will also be appreciated by those of skill in the art, the methods described herein can further comprise thawing the stem cells. In one aspect, the stem cells are thawed rapidly (e.g., placed in a 37° C. water bath) thereby producing thawed stem cells. In other aspects, the thawed stem cells can be cultured in a culture medium. In a particular aspect, the thawed stem cells are cultured in a cell culture medium comprising WJSCs, a cell culture medium that has been conditioned with Wharton's Jelly mesenchymal stem cells (WJSCs) and/or a combination thereof. In particular aspects, the stem cells are thawed by culturing the cells in the cell culture medium for about 6 hours, 12 hours, 24 hours, 30 hours, 36 hours, 42 hours, 48 hours, 54 hours, 60 hours, 66 hours, 72 hours, 8 days, 10 days, 12 days, 14 days, 16 days, 18 days, 20 days, 22 days, 24 days, 26 days 28 days or 30 days, 2 months, etc.

The methods can further comprise expanding the stem cells, for example, either prior to freezing of the stem cells or after freezing and thawing of the stem cells. A variety of methods for expanding stem cells are known (e.g., Fong et al., J Cell Biochem, 113(2):658-668 (2012) which is incorporated herein by reference).

In another aspect, the invention is directed to stem cells producing by the methods described herein. In other aspects, the invention is directed to a pharmaceutical composition comprising the stem cells produced by the methods described herein.

A "pharmaceutical composition" comprises a (one or more) composition or compound described herein as the active ingredient and inert ingredient(s), such as pharmaceutically acceptable excipients, that make up the carrier. Standard pharmaceutical formulation techniques can be employed, such as those described in Remington's Pharmaceutical Sciences, Mack Publishing Company, Easton, Pa. Suitable pharmaceutical carriers for parenteral administration include, for example, sterile water, physiological saline, bacteriostatic saline (saline containing about 0.9% mg/ml benzyl alcohol), phosphate-buffered saline, Hank's solution, Ringer's lactate and the like. Formulations can also include small amounts of substances that enhance the effectiveness of the active ingredient (e.g., emulsifying, solubilizing, pH buffering, wetting agents). Methods of encapsulation compositions (such as in a coating of hard gelatin or cyclodextran) are known in the art. For inhalation, the agent can be solubilized and loaded into a suitable dispenser for administration (e.g., an atomizer or nebulizer or pressurized aerosol dispenser).

EXEMPLIFICATION

Provided below are various aspects of the methods of the invention. As will be appreciated by those of skill in the art, all or some of the steps, in the order or in an alternative order, described herein may be used in the methods of the invention.

Example 1

Materials
Propagation of hWJSCs and Preparation of hWJSC-CM
Human umbilical cords were obtained after informed patient consent and institutional domain specific review board (DSRB) ethical approval. Human Wharton jelly stem cells were derived from the umbilical cords using the method of Fong et al [Fong et al. Reprod Biomed Online, 15:708-718 (2007)].

T75 tissue culture flasks (Thermo Fisher Scientific, Rochester, N.Y.).

hWJSC medium [80% DMEM (high glucose) medium supplemented with 20% fetal bovine serum (FBS) (Biochrom, Berlin, Germany), 1% non-essential amino acids, 2 mM L-glutamine, 0.1 mM β-mercaptoethanol, 1% insulin-transferrin-selenium (ITS), antibiotic/antimycotic mixture (50 IU penicillin, 50 µg/ml streptomycin) (Invitrogen Life Technologies, Carlsbad, Calif.) and 16 ng/ml basic fibroblast growth factor (Millipore Bioscience Research Agents, Temecula, Calif.)].

Incubator (37° C., 5% $CO_2$ in air).

Sorvall Lengend RT+ Centrifuge (Thermo Fisher Scientific, Rochester, N.Y.).

StemSpan Serum Free Expansion medium (StemSpan SFEM, Stem Cell Technologies, Vancouver, BC) supplemented with 2 mM L-glutamine, 1% antibiotic/antimycotic mixture (Invitrogen Life Technologies, Carlsbad, Calif.).

0.22 µM filters (Millipore Bioscience Research Agents, Temecula, Calif.).

Freezing and Thawing

Freezing medium (Experimental) (FME) [24 h-50% hWJSC-CM supplemented with 2 mM L-glutamine, 1% antibiotic/antimyotic mixture (Invitrogen Life Technologies, Carlsbad, Calif.), 40% FBS (HyClone Thermo Scientific, Rochester, N.Y.) and 10% DMSO (Sinopharm Chemical Reagent Co Ltd, Shanghai, China)]

Freezing Medium (Control) (FMC) [50% StemSpan SFEM (StemCell Technologies Vancouver, BC) supplemented with 2 mM L-glutamine, 1% antibiotic/antimyotic mixture (Invitrogen Life Technologies, Carlsbad, Calif.), 40% FBS (HyClone Thermo Fisher Scientific, Rochester, N.Y.) and 10% DMSO (Sinopharm Chemical Reagent Co. Ltd, Shanghai, China)]

1 mL cryovials (Thermo Fisher Scientific, Rochester, N.Y.).

Controlled rate freezer (Planer Kryo10 Series II, Planer PLC, London, UK).

Liquid nitrogen tank
Liquid nitrogen
Water bath

Thawing medium (TM) [IMDM (Invitrogen Life Technologies, Carlsbad, Calif.) supplemented with 20% FBS (HyClone Thermo Fisher Scientific, Rochester, N.Y.), 2 mM L-glutamine, 1% antibiotic/antimycotic mixture (Invitrogen Life Technologies, Carlsbad, Calif.)]

Post-thaw medium (Experimental) (PTME) [24 h-50% hWJSC-CM supplemented with 20% FBS (HyClone Thermo Fisher Scientific, Rochester, N.Y.), 2 mM L-glutamine and 1% antibiotic/antimyotic mixture (Invitrogen Life Technologies, Carlsbad, Calif.)]

Post-thaw medium (Control) (PTMC) ([StemSpan SFEM supplemented with 20% FBS (HyClone Thermo Fisher Scientific, Rochester, N.Y.), 2 mM L-glutamine and 1% antibiotic/antimyotic mixture (Invitrogen Life Technologies, Carlsbad, Calif.]

24 well plates (Thermo Fisher Scientific, Rochester, N.Y.).
Incubator (37° C., 5% $CO_2$ in air)
Expansion of UCB CD34+ Cells Human umbilical cord blood (UCB) CD34+ HSCs were purchased as kits from Stem Cell Technologies, Vancouver, BC. Ethical approval for their purchase and use was given by the National University of Singapore Institutional Review Board (NUS-IRB).

StemSpan SFEM (StemCell Technologies Vancouver, BC, Canada).

CC110 Cytokines Cocktail (StemCell Technologies Vancouver, BC, Canada)

60 mm dishes [Becton Dickson (BD), Franklin Lanes, N.J.]

Incubator (37° C., 5% $CO_2$ in air)
Cell Morphology

Olympus IX70 Inverted fluorescence microscope (Olympus Corporation, Tokyo, Japan)

MTT Cell Proliferation Assay
96 well plate (Thermo Fisher Scientific, Rochester, N.Y.).
StemSpan SFEM (Stem Cell Technologies, Vancouver, BC, Canada) supplemented with 20% FBS (HyClone ThermoScientific, Rochester, N.Y.), 2 mM L-glutamine and 1% antibiotic/antimyotic mixture (Invitrogen Life Technologies, Carlsbad, Calif.)

MTT kit [3-(4,5-dimethylthiazolyl-2)-2,5-diphenyltetrazolium bromide, (MTT) 0.5 mg/ml (Duchefa Biochemie B.V., Haarlem, Netherlands)

Incubator (37° C., 5% $CO_2$ in air)

Dimethylsulfoxide (DMSO) (Sinopharm Chemical Reagent Co. Ltd, Shanghai, China)

Microplate ELISA reader (mQuant, BioTek and Winooski, Vt., USA)

Annexin V-FITC/PI Assay

Phosphate buffered saline without calcium and magnesium [PBS(−)](Invitrogen Life Technologies, Carlsbad, Calif.)

Annexin V binding buffer (10×) (BioVision, Inc., Mountain View, Calif.)

Annexin V-FITC (BioVision, Inc, Mountain View, Calif.)

Propidium iodide (PI) (1 µg/mL) (Invitrogen Life Technologies, Carlsbad, Calif.)

40 µM nylon strainer [Becton Dickson (BD), Franklin Lanes, N.J.]

CyAn™ ADP Analyser (Beckman Coulter, Fullerton, Calif.)

Live/Dead® Assay

PBS(−) (Invitrogen Life Technologies, Carlsbad, Calif.)

Live/Dead® Viability/Cytotoxicity kit for mammalian cells (Invitrogen Life Technologies, Carlsbad, Calif.)

40 µM nylon strainer (Becton Dickson (BD), Franklin Lanes, N.J.)

CyAn™ ADP Analyser (Beckman Coulter, Fullerton, Calif.)

Cell Cycle Assay

70% ethanol

PBS(−)

Propidium iodide (PI) (20 µg/mL) (Invitrogen Life Technologies, Carlsbad, Calif.)

RNase A (100 µg/mL) (AppliChem GmbH, Garmstadt, Germany)

40 µM nylon strainer [Becton Dickson (BD), Franklin Lanes, N.J.]

CyAn™ ADP Analyser (Beckman Coulter, Fullerton, Calif.)

CD34+Analysis

10% normal goat serum (Invitrogen Life Technologies, Carlsbad, Calif.)

Primary anti-human CD34 antibodies (1:100) (Biolegends, San Diego, USA)

Secondary anti-mouse IgG (H+L) Alexa Fluor® 488 secondary antibody (1:750) (Invitrogen Life Technologies, Carlsbad, Calif.)

40 µM nylon strainer [Becton Dickson (BD), Franklin Lanes, N.J.]

CyAn™ ADP Analyser (Beckman Coulter, Fullerton, Calif.)

Colony Forming Unit (CFU) Assay

IMDM supplemented with 20% FBS, L-glutamine and antibiotic/antimyotic mixture (Invitrogen Life Technologies, Carlsbad, Calif.).

MethoCult™ H4435 medium (Stem Cell Technologies, Vancouver, BC)

32G blunt end needle (Stem Cell Technologies, Vancouver, BC)

24 well plates (Thermo Fisher Scientific, Rochester, N.Y.).

Inverted phase contrast microscope (Nikon Instruments, Tokyo, Japan).

Atlas of Hematopoietic Colonies from Cord Blood (Stem Cell Technologies, Vancouver, BC)

CytoSelect™ Hematopoietic Colony Forming Assay (Cell Biolabs, Inc., San Diego, Calif.).

96 well assay plate (Thermo Fisher Scientific, Rochester, N.Y.).

TECAN GENios (TECAN Austria GmBH, Salzburg, Austria)

Methods

Propagation of hWJSCs and Preparation of hWJSC-CM hWJSCs were grown in a T75 tissue culture flask with hWJSC medium until 70% confluence as previously described [Fong et al. Reprod Biomed Online, 15:708-718 (2007)].

hWJSC-CM was prepared as previously described [Fong, J Cell Biochem, 113:658-668 (2012)].

hWJSC medium was replaced with StemSpan SFEM medium supplemented with 2 mM L-glutamine and antibiotic/antimyotic mixture.

hWJSCs were cultured in this medium for 24 h and then separated and filter-sterilized using a 0.22 µM filter.

hWJSC-CM was stored at −20° C. until use.

Preparation of hWJSC-CM was carried out on early hWJSC passages (3P to 5P).

Expansion of Commercial UCB CD34+ Cells

Flow Activated Cell Sorting (FACS) profile given by the company showed that more than 90% of the cells were CD34+.

Expansion of the frozen UCB CD34+ cells was according to the manufacturer's instructions supplied with the kit.

The frozen cells in the cryovial were thawed within 1-2 min using a water bath (37° C.).

6 ml of thawing medium was slowly added drop by drop to the cryovial to prevent osmotic shock to the CD 34+ cells.

The cryovials were then centrifuged, supernatant decanted and cells resuspended in StemSpan SFEM medium supplemented with 2 mM L-glutamine, 1% antibiotic/antimyotic mixture and cytokines cocktail CC110.

UCB CD34+ cells were first equilibrated and grown in this Expansion medium for 3 days before use for freeze-thaw survival experiments.

Freezing and Thawing of UCB CD34+ Cells

UCB CD34+ cells were frozen using slow programmed freezing in a controlled rate freezing machine (Kryo10 Series II) from room temperature at a freezing rate of −1° C. per minute to −120° C. as previously described [Hayakawa et al., Transfusion, 50:2158-2166 (2010)]. Three different UCB samples were evaluated. Each UCB sample was divided into two groups A and B. Group A: Freezing Medium (Control) (FMC); Group B: Freezing medium (Experimental) (FME).

The cryovials were removed at −120° C. and plunged into liquid nitrogen (−196° C.) in a tank for long-term storage.

Cells were maintained at −196° C. for at least 2 weeks before analysis.

Frozen CD34+ cells from Groups A and B were thawed rapidly within 1-2 min in a 37° C. water bath.

3 mL of thawing medium was then added into each cryovial and the cryovial centrifuged at 500×g for 5 min.

The supernatant was then removed and the cell pellets from each of Groups A and B were divided into 2 Subgroups, with each Subgroup having Experimental and Control arms. Subgroup 1: 0 h post-thaw analysis (Analysis done immediately after thawing) (Experimental arm: hWJSC-CM; Control arm: control). Subgroup 2: 72 h post-thaw analysis (Analysis done 72 hours after thawing) (Experimental arm: Thawed cells grown for 72 h in hWJSC-CM; Control arm: Thawed cells grown for 72 h in control medium).

The analyses included cell morphology, cell proliferation assay, CD34+ cell analysis, CFU assay, Annexin V-FITC/PI assay, Live/Dead® Viability assay and Cell Cycle assay.

Results were expressed as mean±SEM and statistically significant differences between groups were calculated using the two-tailed Student's t-test using SPSS Statistic v 17.0 (SPSS, Inc, IL). A p value of <0.05 was considered as statistically significant.

Cell Morphology

Cell pellets from Experimental and Control arms were placed in their respective media and the cell morphology immediately observed.

No distinct morphological differences were observed in the UCB CD34+ cells between the two arms with cells in both arms showing their characteristic spherical shape and size [FIGS. 1A, 1B)].

Thawed cells from Experimental and Control arms were cultured for 72 h in their respective media and morphology observed.

More cellular debris was observed after 72 h culture in the Control compared to the Experimental arms [FIGS. 1C-1F]

Cell Proliferation Assay

Cell pellets from Experimental and Control groups were re-suspended in 100 µL StemSpan SFEM supplemented with 20% FBS, L-glutamine and antibiotic/antimycotic mixture.

10 µL of MTT (final concentration of 0.5 mg/ml) was added to each sample and incubated at 37° C., 5% $CO_2$ in air atmosphere overnight.

The samples were then centrifuged at 1,000×g for 5 min.

The supernatants were then removed and each cell pellet resuspended in 100 µl of DMSO. The cell suspensions were then incubated in the dark for 10 min.

Each sample was dispensed into the wells of a 96 well plate and the intensity of the purple colour was measured at 570 nm absorbance against a reference wavelength of 630 nm using a microplate ELISA reader.

Figures 2A, 2B, 2C, 2D:
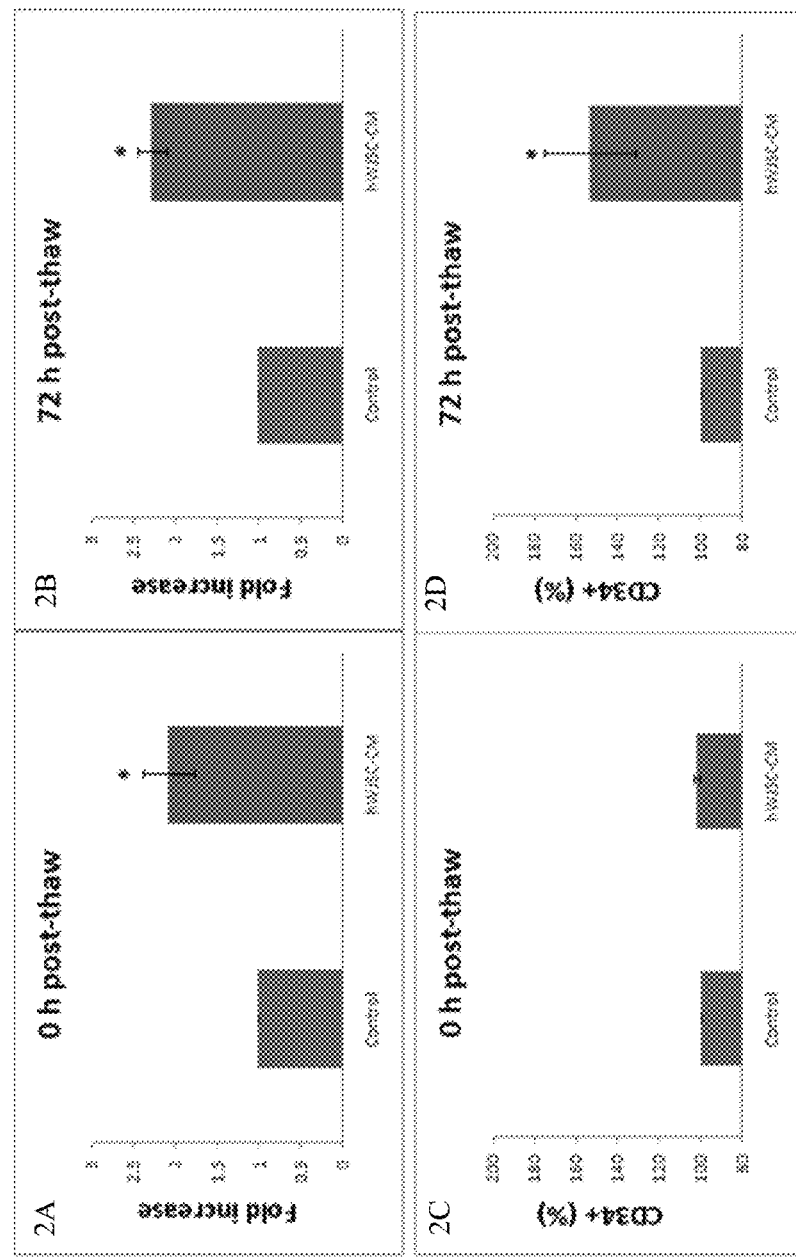
FIGS. 2A-2D. Proliferation rate of CD34+ cells frozen in hWJSC-CM, thawed and grown in hWJSC-CM for 72 h. (2A): Note greater fold increases (normalised to respective controls) of CD34+ cells frozen in hWJSC-CM, thawed and analysed immediately (0 h post-thaw) and; (2B): Note greater fold increases of CD34+ cells after thawing and growing in hWJSC-CM for 72 h (72 h post-thaw). (2C): Note percentage increases (normalised to respective controls) of CD34+ cells frozen in hWJSC-CM, thawed and analysed immediately (0 h post-thaw); and (2D) Note percentage increases of CD34+ cells after thawing and growing in hWJSC-CM for 72 h (72 h post-thaw). Values are mean±SEM of 3 samples with 3 replicates for each sample. Asterisk (*): $p < 0.05$.

A significantly greater number of CD34+ cells survived in hWJSC-CM compared to controls immediately after thawing (2.08±0.3 fold increase) [FIG. 2A].

Significantly greater proliferation rates of CD34+ cells were observed when they were frozen in hWJSC-CM and cultured after thawing for 72 h in hWJSC-CM compared to controls.

The mean±SEM fold increase in CD34+ proliferation rates in samples frozen in hWJSC-CM and cultured in hWJSC-CM after thawing were 2.28±0.17 [FIG. 2B].

CD34+Cell Analysis

Cell pellets from Experimental and Control arms were blocked with 10% NGS to prevent non-specific binding.

The cells were then incubated with primary anti-human CD34 antibody for 30 min followed by secondary anti-mouse IgG(H+ L) antibody in the dark for 30 min.

The cells were washed with PBS (-), re-suspended in 10% NGS and filtered using a 40 µM nylon strainer to remove cell clumps and analyzed with CyAn™ ADP Analyzer.

Greater percentages of CD34+ cells were observed in hWJSC-CM immediately after thawing compared to controls (102±1.17%) [FIG. 2C].

Significantly greater percentages of CD34+ cells were observed when they were frozen in hWJSC-CM and cultured after thawing for 72 h in hWJSC-CM compared to controls.

The mean±SEM percentage in CD34+ cells in samples frozen in hWJSC-CM and cultured in hWJSC-CM after thawing were 153.3±21.99% [FIG. 2D].

CFU Assay

Cell pellets from Experimental and Control arms were re-suspended in 1 mL of IMDM medium supplemented with 20% FBS, L-glutamine and antibiotic/antimycotic mixture.

50 µl of the cell suspension from each group was seeded into each well of a 24-well plate containing 0.5 mL in MethoCultR H4435 medium. The 24-wells plates were incubated at 37° C., 5% CO2 in air atmosphere for 12 days.

Colonies (CFU) that were formed after 12 days were classified based on morphology as described by the Atlas of Hematopoietic Colonies from Cord Blood.

Cells from all groups displayed typical GEMM CFU morphology as described in the literature [FIGS. 3A-3D].

CFU colonies were quantified using the CytoSelect™ Hematopoietic Colony Forming assay.

Briefly, the cells were collected and resuspended in 250 µL IMDM medium supplemented with 20% FBS, L-glutamine and antibiotic/antimycotic mixture.

50 µl of 4× Lysis Buffer/CyQuant® GR dye solution (1:75 dilution) was then added to each sample, mixed, and incubated for 30 min at room temperature.

100 µl of the mixture was added to each well in the 96 well plate and readings were taken with a 485 nm/535 nm filter set using TECAN GENios.

Figures 3A, 3B, 3C, 3D, 3E, 3F:
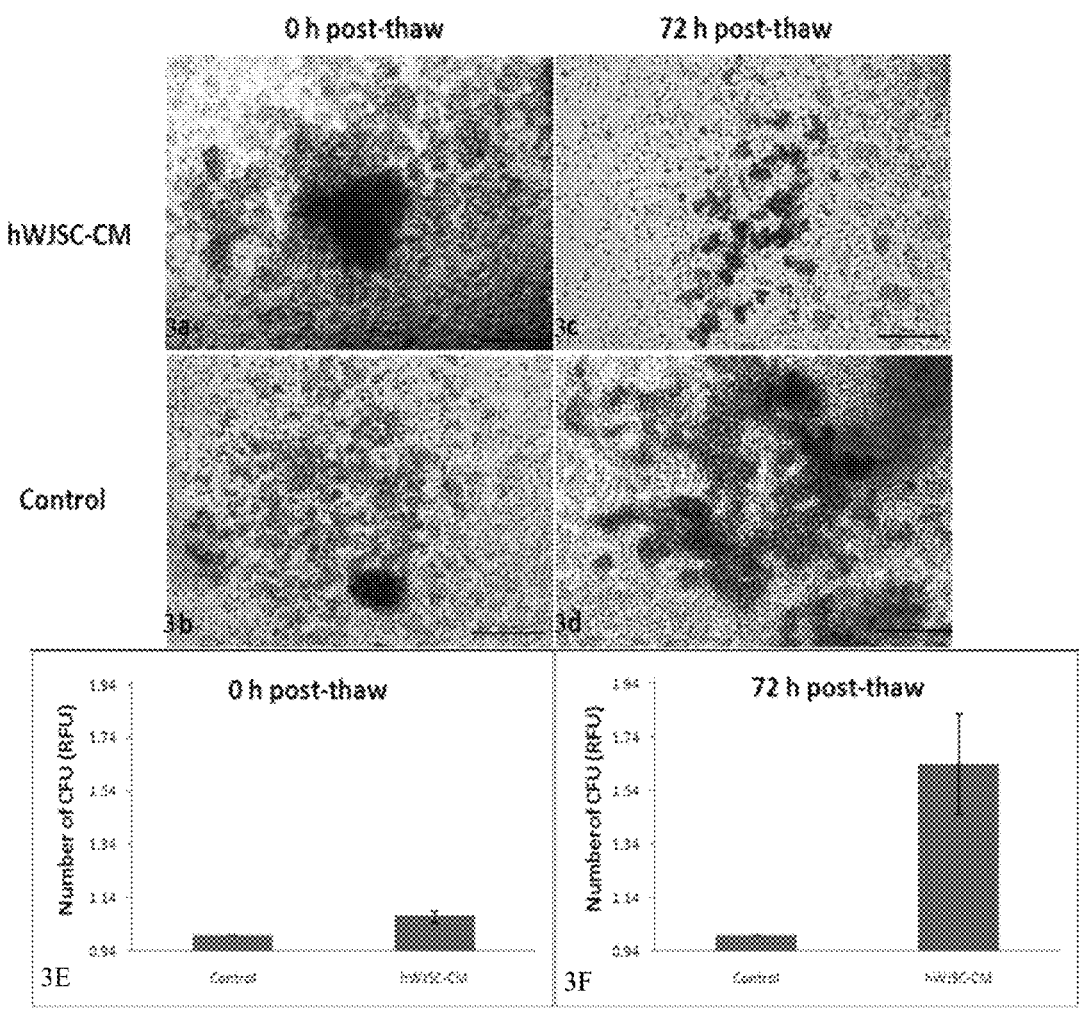
FIGS. 3A-3F: CFU assay of CD34+ cells frozen in hWJSC-CM, thawed and grown in hWJSC-CM for 72 h. (3A): CD34+ cells frozen in hWJSC-CM, thawed and grown on methylcellulose for 12 days showed typical GEMM colonies, (3B): Parallel controls showed similar GEMM colonies. (3C): Similar GEMM colonies were observed for CD34+ cells frozen in hWJSC-CM, thawed and then grown in hWJSC-CM for 72 h. (3D): Parallel controls showed similar GEMM colonies. (3E): Greater number of colonies (normalised to controls) were observed when CD34+ cells were frozen in hWJSC-CM, thawed and grown on methylcellulose; and (3F): Greater number of colonies (normalised to controls) were observed when CD34+ cells were frozen in hWJSC-CM, thawed, grown in hWJSC-CM for 72 h and then grown on methylcellulose. Values are mean±SEM of 3 samples with 3 replicates for each sample.

Cells that were frozen in hWJSC-CM produced more CFUs compared to controls (1.07±0.02) [FIG. 3E].

More CFUs were observed when they were frozen in hWJSC-CM and cultured after thawing for 72 h in hWJSC-CM compared to controls.

The mean±SEM in number of CFUs in samples frozen in hWJSC-CM and cultured in hWJSC-CM for 72 h after thawing were 1.6±0.19 [FIG. 3F].

Annexin V-FITC/PI Assay

Cell pellets from Experimental and Control arms were washed with Annexin V binding buffer (1×).

The cells were stained with 0.15 µg/mL Annexin V-FITC and counterstained with 1 µg/mL PI at room temperature for 15 min in the dark.

The cells were then filtered using a 40 µM nylon strainer to remove cell clumps and analyzed with a CyAn™ ADP Analyzer.

Figures 4A, 4B, 4C, 4D:
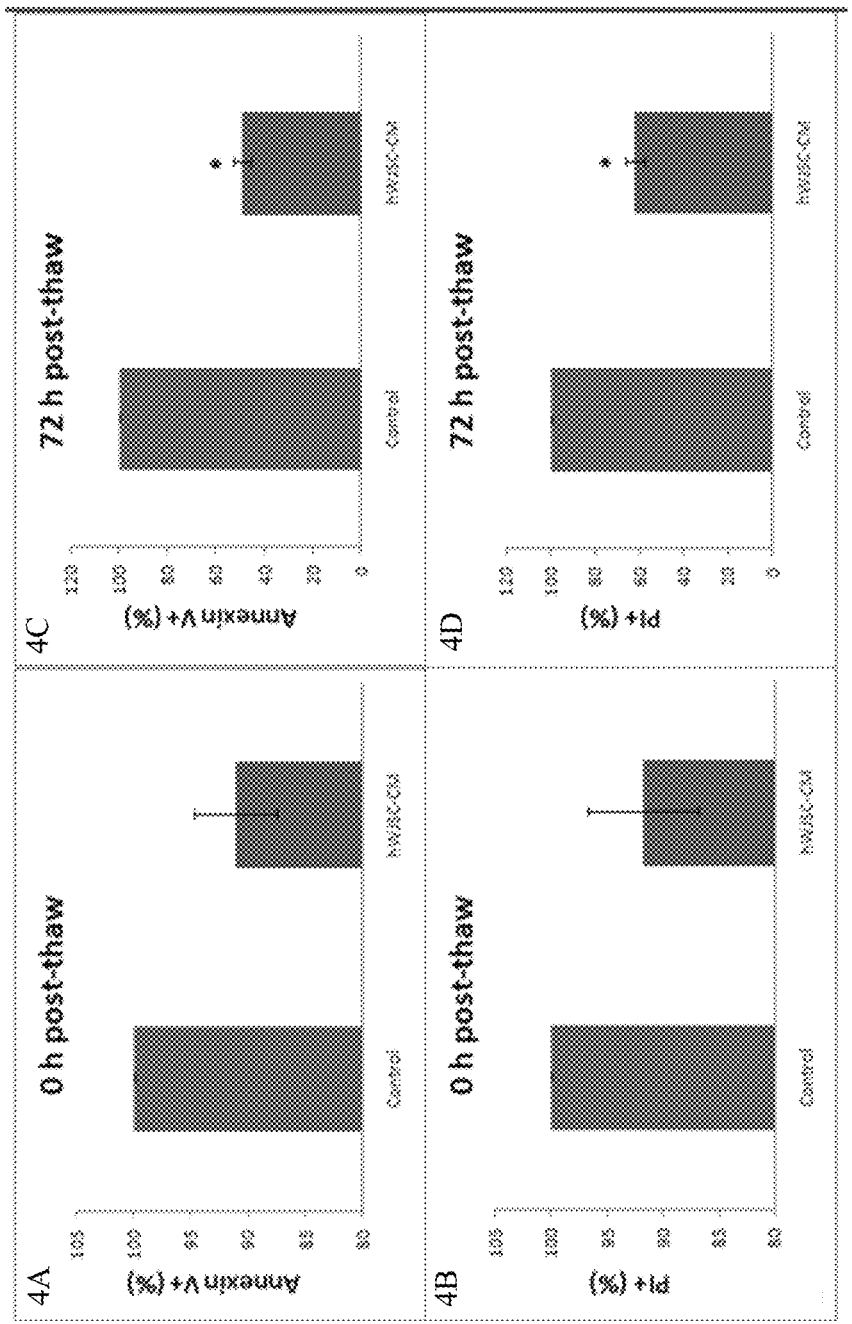
FIGS. 4A-4D: Annexin V/PI assay of CD34+ cells frozen in hWJSC-CM, thawed and grown in hWJSC-CM for 72 h. (4A): Lower percentages of apoptotic cells (Annexin V+) (normalised to controls) were observed when CD34+ cells were frozen in hWJSC-CM, thawed and analysed immediately (0 h post-thaw). (4B): Lower percentages of necrotic cells (PI+) (normalised to controls) were observed when CD34+ cells were frozen in hWJSC-CM, thawed and analysed immediately (0 h post-thaw). (4C): Lower percentages of apoptotic cells (Annexin V+) (normalised to controls) were observed when CD34+ cells were frozen in hWJSC-CM, thawed and grown in hWJSC-CM for 72 h (72 h post-thaw). (4D): Lower percentages of necrotic cells (PI+) (normalised to controls) were observed when CD34+ cells were frozen in hWJSC-CM, thawed and grown in hWJSC-CM for 72 h (72 h post-thaw). Values are mean±SEM of 3 replicates for each sample. Asterisk (*): $p < 0.05$.

Cells frozen in hWJSC-CM had lower percentages of Annexin V+ cells compared to controls (91.06±3.63%) [FIG. 4A].

Cells frozen in hWJSC-CM had lower percentages of PI+ cells as compared to controls (91.80±5.01%) [FIG. 4B].

Significantly lower percentages of Annexin V+ and PI+ CD34+ cells were observed when they were thawed and cultured for 72 h in hWJSC-CM compared to controls. The mean±SEM percentages for Annexin V+ and PI+ cells were 49.2±3.59% and 62.0±4.30% respectively compared to controls [FIG. 4C, 4D].

Live/Dead® Viability Assay

The staining solution was prepared by first mixing 1 µl of component A from the manufacturer's kit with 79 µl of DMSO. 1 µL of this working solution and 2 µL of component B (in the kit) were then mixed with 500 µl of PBS (-).

Cell pellets from Experimental and Control arms were washed with PBS (-).

Cells from each arm were stained with the staining solution and incubated at room temperature for 15 min in the dark.

Cells were then filtered using a 40 µM nylon strainer to remove cell clumps before analysis with CyAn™ ADP Analyzer.

Dead cells were stained red while live cells stain green. Live/dead percentages represented cell viability.

Figures 5A, 5B, 5C, 5D, 5E, 5F:
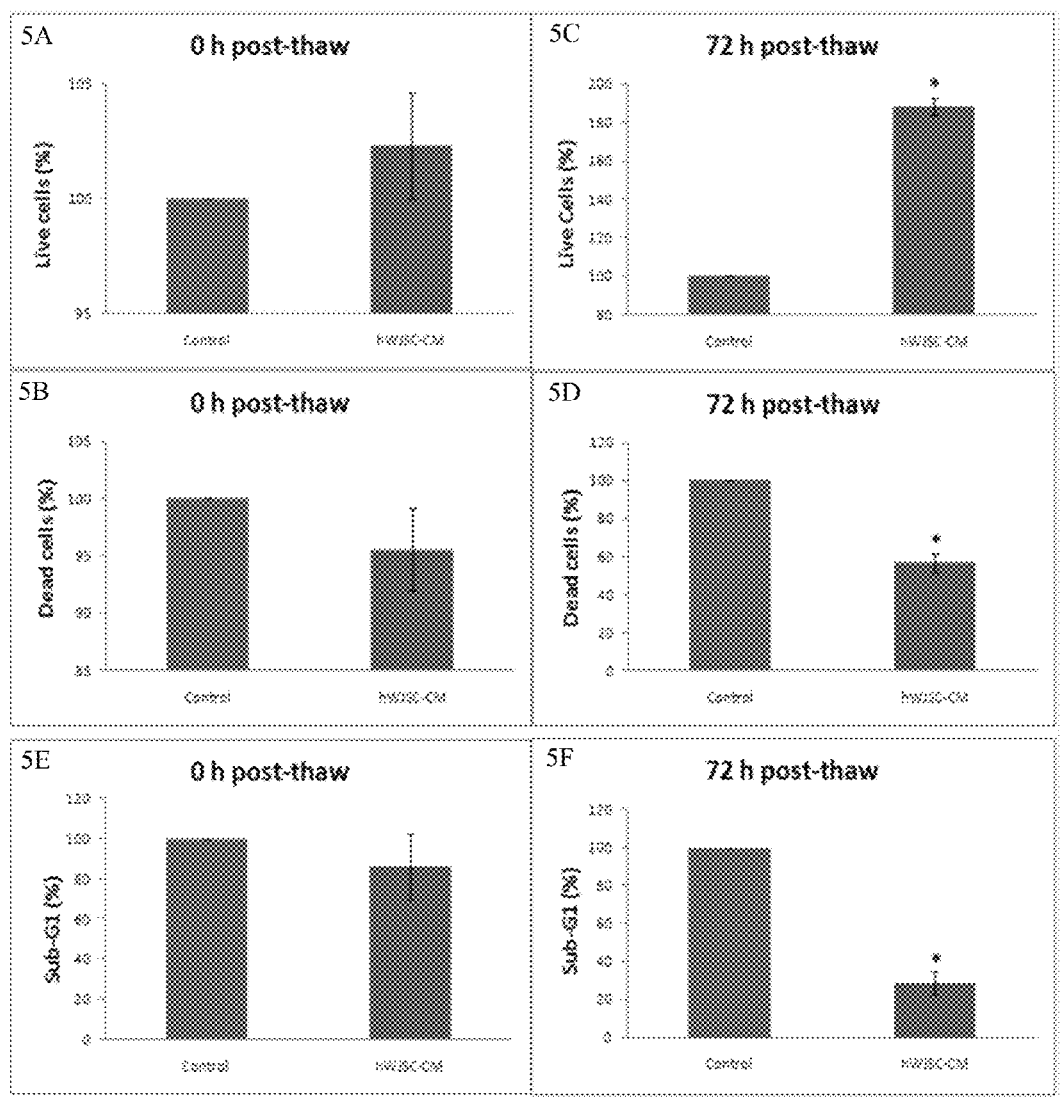
FIGS. 5A-5F: Live/Dead viability and cell cycle analysis of CD34+ cells frozen in hWJSC-CM, thawed and grown in hWJSC-CM for 72 h. (5A): Higher percentages of live cells (normalised to controls) were observed when CD34+ cells were frozen in hWJSC-CM, thawed and analysed immediately (0 h post-thaw). (5B): Lower percentages of dead cells (normalised to controls) were observed when CD34+ cells were frozen in hWJSC-CM thawed and analysed immediately (0 h post-thaw). (5C): Higher percentages of live cells (normalised to controls) were observed when CD34+ cells were frozen in hWJSC-CM, thawed and grown in hWJSC-CM for 72 h (72 h post-thaw). (5D): Lower percentages of dead cells (normalised to controls) were observed when CD34+ cells were frozen in hWJSC-CM, thawed and grown in hWJSC-CM for 72 h (72 h post-thaw). (5E): Lower percentages of cells with fragmented DNA (sub G1 phase) (normalised to controls) were observed when CD34+ cells were frozen in hWJSC-CM, thawed and analysed immediately (0 h post-thaw); and (5F): Lower percentages of cells with fragmented DNA (sub G1 phase) (normalised to controls) were observed when CD34+ cells were frozen in hWJSC-CM, thawed and grown in hWJSC-CM for 72 h (72 h post-thaw). Values are mean±SEM of 3 samples with 3 replicates for each sample. Asterisk (*): p<0.05.

Greater percentages of live cells (102.3±2.32%) were observed in samples frozen in hWJSC-CM compared to controls [FIG. 5A].

Lower percentages of dead cells (95.6±3.61%) were observed in samples frozen in hWJSC-CM compared to controls [FIG. 5B].

Significantly higher percentages of live cells were observed when they were thawed and cultured for 72 h in hWJSC-CM compared to controls. The mean±SEM percentage of live cells was 188.2±4.76% compared to controls [FIG. 5C].

Significantly lower percentages of dead cells were observed when they were thawed and cultured for 72 h in hWJSC-CM compared to controls. The mean±SEM percentage of dead cells was 56.6±5.06% compared to controls [FIG. 5D].

Cell Cycle Assay

Cell pellets from Experimental and Control arms were fixed in 70% ethanol overnight at −20° C.

The cells were washed with PBS (−) and stained by incubating with 20 μg/mL PI and 100 μg/mL RNase A for 15 min at 37° C., 5% $CO_2$ in air atmosphere.

The cells were then filtered using a 40 μM nylon strainer to remove cell clumps before analysis with a CyAn™ ADP Analyzer.

There were lesser percentage of cells with fragmented DNA (Sub-G1 phase) in samples frozen in hWJSC-CM compared to controls (86.1±16.26%) [FIG. 5E].

Significantly lower percentages of cells with fragmented DNA were also observed when thawed CD34+ cells were cultured for 72 h in hWJSC-CM. The mean±SEM percentages of cells in sub-G1 phase were 28.6±5.74% in hWJSC-CM compared to controls [FIG. 5F].

Example 2

Freezing of Umbilical Cord Blood (UCB) CD34+ Cells in Xeno-Free Freezing Media

Methods

Figure 6:
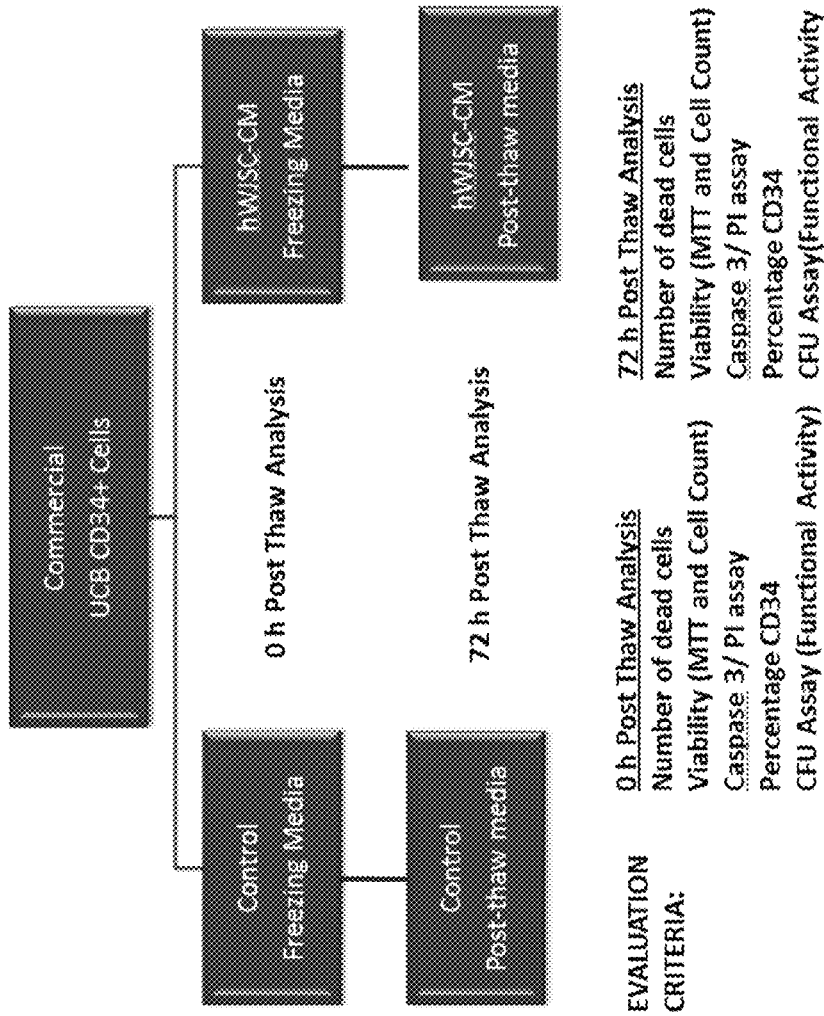
FIG. 6 is a schematic of the Experimental Design of Xeno-Free Freezing Media.
Figures 8A, 8B, 8C, 8D:
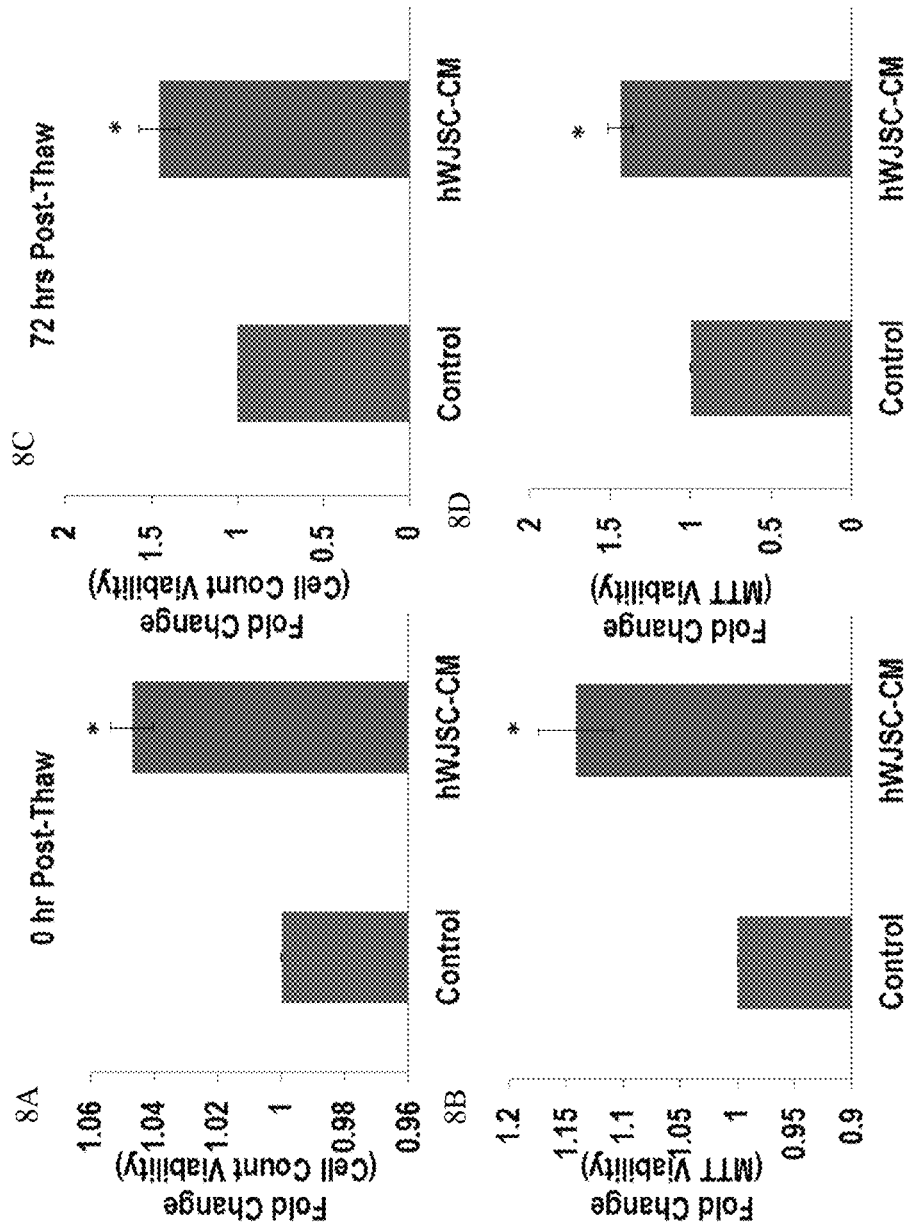
FIGS. 8A-8D: Cell viability of CD34+ cells frozen in hWJSC-CM, thawed and grown in hWJSC-CM for 72 h. (8A-8B): Note greater fold increases (normalised to respective controls) of CD34+ cells frozen in hWJSC-CM, thawed and analysed immediately (0 h post-thaw) using (8A) trypan blue cell counting and (8B) MTT assay and; (8C-8D): Note greater fold increases of CD34+ cells' viability after thawing and growing in hWJSC-CM for 72 h (72 h post-thaw) using (8C) trypan blue cell counting and (8D) MTT assay. Values are mean±SEM of 1 samples with 3 replicates. Asterisk (*): p<0.05.
Figures 9A, 9B, 9C, 9D:
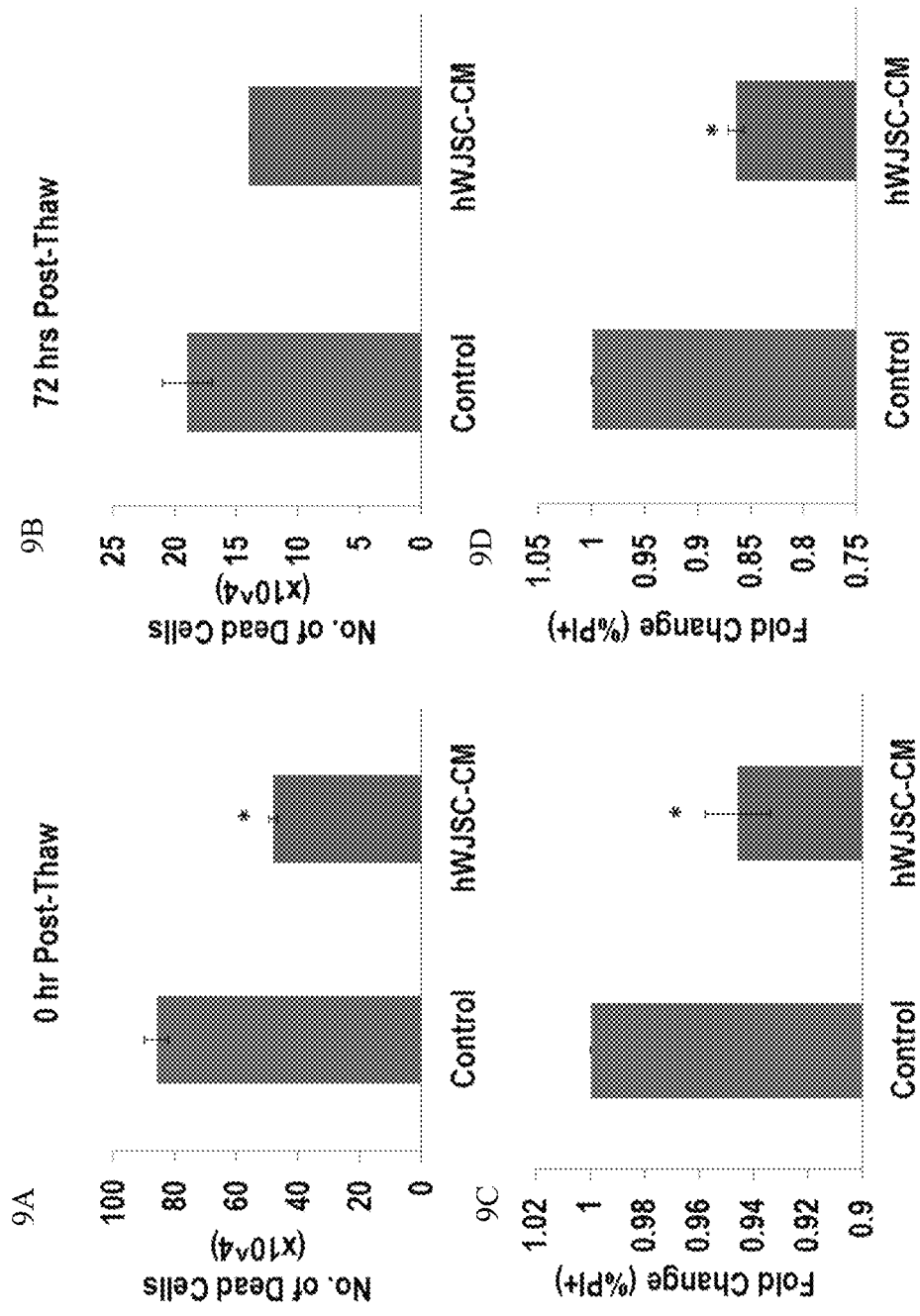
FIGS. 9A-9D: Cell death analysis of CD34+ cells frozen in hWJSC-CM, thawed and grown in hWJSC-CM for 72 h. (9A) Note lower number of dead cells (normalised to controls) were observed when CD34+ cells were frozen in hWJSC-CM, thawed and analysed immediately (0 h post-thaw) and (9B) or after growing for 72 h (72 h post thaw) (9C) Lower percentages of dead cells (PI+) (normalised to controls) were observed when CD34+ cells were frozen in hWJSC-CM, thawed and analysed immediately (0 h post thaw) or (9D) thawed and grown in hWJSC-CM for 72 h (72 h post-thaw). Values are mean±SEM of 1 samples with 3 replicates. Asterisk (*): p<0.05.
Figures 10A, 10B:
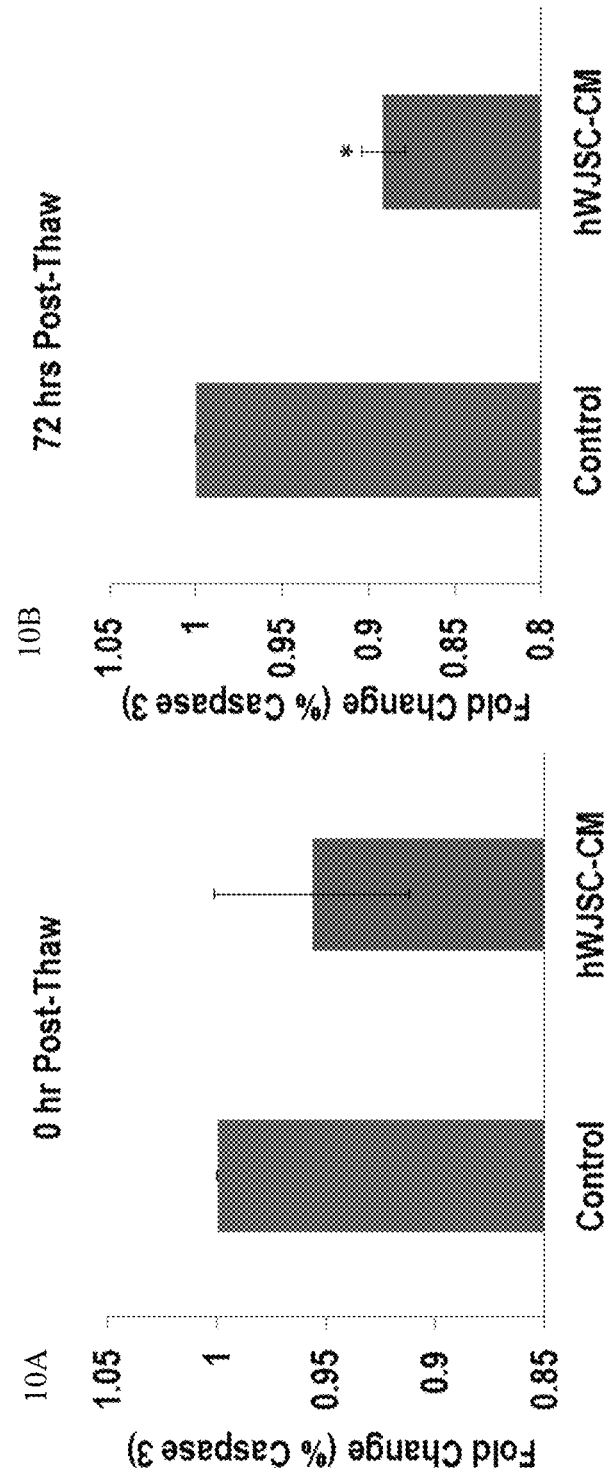
FIGS. 10A-10B: Apoptosis of CD34+ cells frozen in hWJSC-CM, thawed and grown in hWJSC-CM for 72 h. (10A) Note lower percentages (normalised to controls) of caspase 3+ cells were observed when CD34+ cells were frozen in hWJSC-CM, thawed and analysed immediately (0 h post-thaw) or (10B) thawed and grown in hWJSC-CM for 72 h (72 h post thaw). Values are mean±SEM of 1 samples with 3 replicates. Asterisk (*): p<0.05.
Figures 11A, 11B:
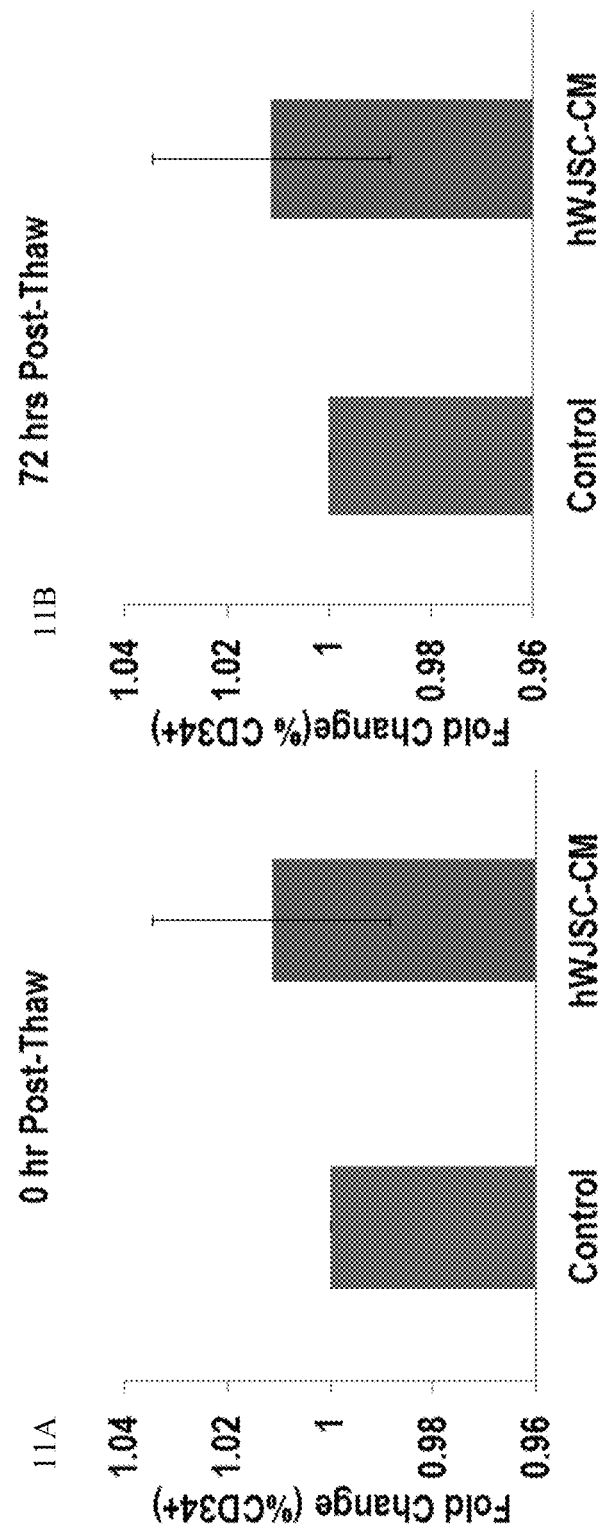
FIGS. 11A-11B:. Percentage of CD34+ cells frozen in hWJSC-CM, thawed and grown in hWJSC-CM for 72 h. (11A) Note percentage increases (normalised to respective controls) of CD34+ cells frozen in hWJSC-CM, thawed and analysed immediately (0 h post-thaw) or (11B) thawed and grown in hWJSC-CM for 72 h (72 h post-thaw). Values are mean±SEM of 1 samples with 3 replicates. Asterisk (*): p<0.05.

See FIGS. 6 and 7 for a schematic of the experimental design.

UCB CD34+ cells were frozen using slow programmed freezing in a controlled rate freezing machine (Kryo10 Series II) from room temperature at a freezing rate of −1° C. per minute to −120° C. Three different UCB samples were evaluated. Each UCB sample was frozen in two different freezing media (Groups A and B). Group A: Freezing Medium (Control) (FMC); Group B: Freezing medium (Experimental) (hWJSC-CM).

Group A freezing medium (Control) (FMC) comprised of StemSpan SFEM supplemented with 1% L-glutamine, 1% antibiotic/antimycotic mixture, 40% of 25% human serum albumin (HSA) and 10% DMSO.

Group B freezing medium (Experimental) (hWJSC-CM) comprised of 50% 24 hr hWJSC-CM in StemSpan SFEM supplemented with 1% L-glutamine, 1% antibiotic/antimycotic mixture, 40% of 25% human serum albumin (HSA) and 10% DMSO.

The cryovials were removed at −120° C. and plunged into liquid nitrogen (−196° C.) in a tank for long-term storage.

Cells were maintained at −1960 C for at least 24 hours before analysis.

Frozen CD34+ cells from Groups A and B were thawed rapidly within 1-2 min in a 37° C. water bath.

3 mL of thawing medium (IMDM supplemented with 20% FBS) was then added into each cryovial and the cryovial centrifuged at 500×g for 5 min.

The supernatant was then removed and the cell pellets from each of Groups A and B were divided into 2 Subgroups, with each Subgroup having Experimental and Control arms. Subgroup 1: 0 h post-thaw analysis (Analysis done immediately after thawing) (Experimental arm: hWJSC-CM; Control arm: control). Subgroup 2: 72 h post-thaw analysis (Analysis done 72 hours after thawing) (Experimental arm: Thawed cells grown for 72 h in hWJSC-CM; Control arm: Thawed cells grown for 72 h in control medium). Control medium comprised of StemSpan SFEM supplemented with 20% FBS 1% L-glutamine, 1% antibiotic/antimycotic mixture and hWJSC-CM comprises of 24 hr hWJSC-CM supplemented with 20% FBS 1% L-glutamine, 1% antibiotic/antimycotic mixture.

The thaw-survival analyses included viable cell counts (Trypan blue staining), MTT assay, Caspase 3 assay, CD34+ staining and Colony forming unit (CFU) assay. Results were expressed as mean±SEM and statistically significant differences between groups were calculated using the two-tailed Student's t-test using SPSS Statistic v 17.0 (SPSS, Inc, IL). A p value of <0.05 was considered as statistically significant See the results in FIGS. 8A-8D, 9A-9D, 10A-10B and 11A-11B.

The teachings of all patents, published applications and references cited herein are incorporated by reference in their entirety.

While this invention has been particularly shown and described with references to example embodiments thereof, it will be understood by those skilled in the art that various changes in form and details may be made therein without departing from the scope of the invention encompassed by the appended claims.

What is claimed:

1. A method of freezing CD34+ stem cells, comprising:
   a) introducing the stem cells into a cell culture medium that has been conditioned with Wharton's Jelly mesenchymal stem cells (WJSCs), thereby producing a stem cell culture; and b) slowly freezing the stem cell culture at a rate that maintains stem cell viability, thereby freezing the stem cells.

2. The method of claim 1 wherein the cell culture medium has been conditioned with WJSCs for about 2 hours, 4 hours, 6 hours, 8 hours, 10 hours, 12 hours, 14 hours, 16 hours, 18 hours, 20 hours, 22 hours, 24 hours, 26 hours, 28 hours, 30 hours, 32 hours, 34 hours, 36 hours, 38 hours, 40 hours, 42 hours, 44 hours, 46 hours, 48 hours, 50 hours, 52 hours, 54 hours, 56 hours, 58 hours, 60 hours, 62 hours, 64 hours, 66 hours, 68 hours, 70 hours, 72 hours, 74 hours, 76 hours, 78 hours, 80 hours, 82 hours, 84 hours, 86 hours, 88 hours, 90 hours, 92 hours, 94 hours or 96 hours.

3. The method of claim 1 wherein the cell culture medium is about 5% v/v, 10% v/v, 15% v/v, 20% v/v, 25% v/v, 30% v/v, 35% v/v, 40% v/v, 45% v/v, 50% v/v, 55% v/v, 60% v/v, 65% v/v, 70% v/v, 75% v/v, 80% v/v, 85% v/v, 90% v/v, 95% v/v or 100% v/v.

4. The method of claim 1 wherein the cell culture medium further comprises one or more cryoprotectants, cell culture supplements, amino acids, antibiotics, antimyotics or combinations thereof.

5. The method of claim 4 wherein the one or more cryoprotectants comprises dimethyl sulfoxide (DMSO), glycerol, ethylene glycol or combinations thereof.

6. The method of claim 4 wherein the one or more cell culture supplements comprises serum, serum replacement, albumin or combinations thereof.

7. The method of claim 6 wherein the serum is bovine serum, fetal bovine serum, human serum, serum replacement, human serum albumin or combinations thereof.

8. The method of claim 4 wherein the one or more amino acids comprise alanine, arginine, asparagines, aspartic acid, cysteine, glutamine, glutamic acid, glycine, histidine, isoleucine, leucine, lysine, methionine, phenylalanine, proline, serine, threonine, tryptophan, tyrosine, valine or combinations thereof.

9. The method of claim 4 wherein the one or more antibiotics comprises penicillin, streptomycin, gentamycin or combinations thereof.

10. The method of claim 4 wherein the one or more antimyotics comprises amphotericin B.

11. The method of claim 1 wherein the stem cells are slowly frozen to about −100° C., −110° C., −120° C., −130° C., −140° C. or −150° C.

12. The method of claim 1 wherein the stem cells are slowly frozen using a freezing rate of about −0.5° C. per minute, −1° C. per minute, −1.5° C. per minute, −2° C. per minute, −2.5° C. per minute, −3° C. per minute, −3.5° C. per minute, −4° C. per minute, −4.5° C. per minute or −5° C. per minute.

13. The method of claim 1 further comprising storing the stem cells.

14. The method of claim 13 wherein the stem cells are stored in a liquid phase of nitrogen or in a vapor phase of nitrogen.

15. The method of claim 1 further comprising thawing the stem cells.

16. The method of claim 15 wherein the stem cells are thawed in a 37° C. water bath.

17. The method of claim 15 wherein the stem cells are thawed and cultured in a cell culture medium that has been conditioned with Wharton's Jelly mesenchymal stem cells (WJSCs).

18. The method of claim 17 wherein the stem cells are cultured in the cell culture medium for about 6 hours, 12 hours, 24 hours, 2 days, 4 days, 6 days, 8 days, 10 days, 12 days, 14 days, 16 days, 18 days, 20 days, 22 days, 24 days, 26 days 28 days or 30 days.

19. The method of claim 1 wherein the stem cells are obtained from bone marrow, cord blood, peripheral blood, blood from placenta or a combination thereof.

20. The method of claim 1 wherein the stem cells and the WJSCs are obtained from different individuals.

21. The method of claim 1 wherein the stem cells and WJSCs are obtained from the same individual.

22. The method of claim 1 wherein the cell culture medium is conditioned with the WJSCs that are obtained from the same source as the stem cells.

23. The method of claim 1 wherein the stem cells are human stem cells.

24. The method of claim 23 wherein the cell culture medium comprises human serum.

25. The method of claim 23 wherein the cell culture medium comprises human serum albumin.

26. The method of claim 25 wherein the human serum albumin is recombinant human serum albumin or fraction V.

27. The method of claim 23 wherein the cell culture medium comprises human serum replacement.

28. The method of claim 1 wherein the WJSCs are human WJSCs.

29. The method of claim 1 wherein the method further comprises expanding the stem cells.

30. The method of claim 29 wherein the stem cells are expanded prior to freezing of the stem cells.

31. The method of claim 29 wherein the stem cells are expanded after freezing and thawing of the stem cells.

32. The method of Claim 29 wherein the stem cells are expanded in a cell culture medium comprising Wharton's Jelly mesenchymal stem cells (WJSCs), a cell culture medium that has been conditioned with WJSCs, or a combination thereof.

33. A method of freezing CD34+ stem cells, comprising:
a) introducing the stem cells and a cell culture medium that has been conditioned with Wharton's Jelly mesenchymal stem cells (WJSCs) into a cryovial, thereby producing a stem cell culture; and
b) freezing the stem cell culture at a rate of about −0.5° C. per minute, −1 ° C. per minute, −1.5° C. per minute, −2° C. per minute, −2.5° C. per minute, −3° C. per minute, −3.5° C. per minute, −4° C. per minute, −4.5° C. per minute or −5° C. per minute, thereby freezing the stem cells.

34. Frozen, isolated CD34+stem cells in a culture medium that has been conditioned with Wharton's Jelly mesenchymal stem cells (WJSCs) wherein the culture medium further comprises a cryoprotectant selected from dimethyl sulfoxide (DMSO), glycerol, ethylene glycol or combinations thereof.

* * * * *